US008193500B2

(12) United States Patent
Iwasaki et al.

(10) Patent No.: US 8,193,500 B2
(45) Date of Patent: Jun. 5, 2012

(54) DISCRIMINATION FILTERING DEVICE, DISCRIMINATION METHOD OF OBJECT, AND DESIGNING METHOD OF FILTERS FOR DISCRIMINATION FILTERING DEVICE

(75) Inventors: Takashi Iwasaki, Itami (JP); Masaharu Mogi, Yokohama (JP); Shigeki Nakauchi, Toyohashi (JP)

(73) Assignees: National University Corporation Toyohashi University of Technology, Toyohashi-shi (JP); Sumitomo Electric Industries, Ltd., Osaka-shi (JP)

( * ) Notice: Subject to any disclaimer, the term of this patent is extended or adjusted under 35 U.S.C. 154(b) by 0 days.

(21) Appl. No.: 12/935,856

(22) PCT Filed: Mar. 27, 2009

(86) PCT No.: PCT/JP2009/056338
§ 371 (c)(1),
(2), (4) Date: Sep. 30, 2010

(87) PCT Pub. No.: WO2009/123068
PCT Pub. Date: Oct. 8, 2009

(65) Prior Publication Data
US 2011/0026029 A1    Feb. 3, 2011

(30) Foreign Application Priority Data

Apr. 1, 2008    (JP) .................................. 2008-095311

(51) Int. Cl.
*G01J 5/00* (2006.01)
(52) U.S. Cl. .................................................... 250/338.1
(58) Field of Classification Search .......... 250/330–335, 250/336.1, 336.2, 337, 338.1–338.5, 339.01–339.15, 250/340, 341.1–341.8, 342–353
See application file for complete search history.

(56) References Cited

U.S. PATENT DOCUMENTS

| 4,840,706 | A | * | 6/1989 | Campbell | 162/198 |
|---|---|---|---|---|---|
| 5,001,346 | A | | 3/1991 | Barkhoudarian | |
| 5,672,874 | A | * | 9/1997 | Fujii et al. | 250/343 |
| 6,252,189 | B1 | * | 6/2001 | Campbell | 209/581 |
| 7,840,360 | B1 | * | 11/2010 | Micheels et al. | 702/25 |

FOREIGN PATENT DOCUMENTS

CA    964487 A1    3/1975

(Continued)

OTHER PUBLICATIONS

Kirkpatrick et al., "Optimization by Simulated Annealing", Science, vol. 220, No. 4598, pp. 671-680, 1983.

(Continued)

*Primary Examiner* — Kiho Kim
(74) *Attorney, Agent, or Firm* — Venable LLP; Michael A. Sartori; Christopher Ma

(57) ABSTRACT

A discrimination filtering device includes a filter and a filter having different pass bands, a detection unit, a processing unit, and a result output unit. The detection unit detects an electromagnetic wave from an object that is the target of identification through the filters. The pass band of the filters is designed to be suitable for object discrimination. The processing unit substitutes the output from the detection unit into a discrimination function determined based on the pass band of the filters and the teaching spectrum obtained in advance to infer the group which the object belongs to based on the substituted result.

17 Claims, 21 Drawing Sheets

FOREIGN PATENT DOCUMENTS

| | | |
|---|---|---|
| CN | 1779461 A | 5/2006 |
| JP | 47009000 A | 5/1972 |
| JP | 56103851 A | 8/1981 |
| JP | 56103853 A | 8/1981 |
| JP | 63161935 A | 7/1988 |
| JP | 2240546 A | 9/1990 |
| JP | 2284045 A | 11/1990 |
| JP | 10099288 A | 4/1998 |
| JP | 2002345760 A | 12/2002 |
| JP | 2003169788 A | 6/2003 |
| JP | 2006226775 A | 8/2006 |

OTHER PUBLICATIONS

Watanabe et al., "Neighborhood Cultivation Genetic Algorithm for Multi-objective Optimization Problems", Information Processing Society of Japan, vol. 43, pp. 183-198, 2002.

Hiromi Hirano, "Genetic Algorithm and Genetic Programming", Personal Media Co., Ltd., Title Page, Colophon and Table of Contents only and the English Translation Thereof, 2000.

Tadashi Kuroiwa, "Trade-off Analysis Method", Toshiba Review, vol. 60, No. 1, pp. 48-51, 2005.

* cited by examiner

DISCRIMINATION FILTERING DEVICE, DISCRIMINATION METHOD OF OBJECT, AND DESIGNING METHOD OF FILTERS FOR DISCRIMINATION FILTERING DEVICE

TECHNICAL FIELD

The present invention relates to a spectroscopic measurement technique of reflectance, particularly the technique of discriminating among a plurality of types of specimens based on spectral results.

BACKGROUND ART

Various approaches for examining the property of specimens and/or for discrimination among a plurality of types of specimens have been developed.

For example, Japanese Patent Laying-Open No. 2003-169788 (Patent Document 1) and Japanese Patent Laying-Open No. 10-99288 (Patent Document 2) disclose an apparatus for measuring the moisture content of skin. The apparatuses disclosed in these documents measure the amount of moisture in skin taking advantage of the fact that the electrostatic capacitance of skin differs depending upon the moisture content of skin.

Further, an apparatus for image-processing a skin picture to quantify skin disorder is disclosed in Japanese Patent Laying-Open No. 63-161935 (Patent Document 3).

Japanese Patent Laying-Open No. 2002-345760 (Patent Document 4) discloses a method and apparatus for estimating the relative depth of the site where melanin is present from the surface of the skin based on a combination of spectroscopic images in three wavelengths.

Patent Document 1: Japanese Patent Laying-Open No. 2003-169788
Patent Document 2: Japanese Patent Laying-Open No. 10-99288
Patent Document 3: Japanese Patent Laying-Open No. 63-161935
Patent Document 4: Japanese Patent Laying-Open No. 2002-345760

DISCLOSURE OF THE INVENTION

Problems to be Solved by the Invention

The usage of spectroscopic technique allows a plurality of types of specimens to be discriminated, not limited to the aforementioned measurement of skin condition.

Specimen discrimination utilizing spectroscopic technique will be described hereinafter with reference to FIG. 1. Reflectance spectra 1a, 1b, 1c and 1d of four different specimens are shown in FIG. 1.

These spectra exhibit different reflectance in the vicinity of a wavelength $\lambda_1$ in FIG. 1. Therefore, by taking measurements of the specimens at wavelength $\lambda_1$, the type of the specimen can be identified from the obtained measurements in an ideal situation.

In practice, variation (disturbance) resulting from the ambient environment is generally generated in the measurement results, which are often so great that the difference in spectrum between the specimens is obscured. It was not possible to conduct discrimination of the specimen through the aforementioned simple method in such a case.

In conventional specimen discrimination approaches, complicated processing was required to eliminate the influence of such variation. For example, the variation was compensated for by obtaining the measurements of respective wavelength, and then yielding the first derivative and second derivative for the wavelength in the spectrum, or by using the measurement results of a reference wavelength ($\lambda_2$ in FIG. 1) that is expected to be absent of difference in the measurement results depending on specimens.

The present invention is directed to solving the aforementioned problems. An object of the present invention is to provide a device that allows discriminant analysis of an object readily.

Means for Solving the Problems

According to an aspect of the present invention, a discrimination filtering device includes a first filter with a first pass band, a second filter with a second pass band encompassing the first pass band, a detection unit for detecting an electromagnetic wave output from an object and passed through one of the first and second filters to output a first signal and a second signal corresponding to the intensity of the electromagnetic wave from the object of interest, and an analysis unit for performing a discriminant analysis of the object of interest based on the first signal normalized by an integral of the second signal.

Preferably, the analysis unit performs the discriminant analysis of the object of interest based on a difference between a logarithm of an integral of the first signal and a logarithm of the integral of the second signal.

Preferably, the analysis unit performs the discriminant analysis of the object of interest based on a value obtained by substituting the first signal and the second signal into a discrimination function determined based on the first pass band and the second pass band.

Preferably, the first pass band and the second pass band include a near infrared region.

Preferably, the analysis unit identifies two or more types of substances classified by type.

Preferably, the analysis unit identifies water from another substance.

Preferably, the analysis unit evaluates and identifies moisture content at the surface of or inside a substance.

Preferably, the discrimination filtering device further includes a wave source for emitting an electromagnetic wave. The detection unit detects the electromagnetic wave output from the object of interest receiving the electromagnetic wave output from the wave source.

Further preferably, the wave source is an LED.

Further preferably, the detection unit detects an electromagnetic wave output from the wave source and passed through the object of interest.

Further preferably, the detection unit detects an electromagnetic wave output from the wave source and reflected from the object of interest.

Preferably, the detection unit includes at least one element converting an electromagnetic wave into an electric signal.

Preferably, the detection unit includes a plurality of elements converting an electromagnetic wave into an electric signal. Each of the plurality of elements is aligned one-dimensionally.

Preferably, the detection unit includes an image sensing element having elements aligned two-dimensionally. Each element converts an electromagnetic wave into an electric signal.

According to another aspect of the present invention, a discrimination method of an object of interest includes the steps of: detecting an electromagnetic wave output from the object of interest and passed through a first filter with a first pass band to output a first signal corresponding to an intensity of the electromagnetic wave passed through the first filter; detecting an electromagnetic wave output from the object of interest and passed through a second filter with a second pass band encompassing the first pass band to output a second signal corresponding to the intensity of the electromagnetic wave passed through the second filter; and performing a discriminant analysis of the object of interest based on the first signal normalized by an integral of the second signal.

According to a further aspect of the present invention, a designing method of filters for a discrimination filtering device includes the steps of: setting a transmission property for each of a plurality of filters; generating a discrimination function used in discriminating an object of interest by the discrimination filtering device from the set transmission property and a teaching spectrum of a plurality of samples; calculating an error rate of erroneously discriminating a sample when the discrimination function is used; modifying the transmission property; regenerating the discrimination function from the modified transmission property and teaching spectrum; calculating the error rate for the regenerated discrimination function; and obtaining a transmission property that provides the smallest error rate from the set transmission property and modified transmission property.

Preferably, the teaching spectrum includes a spectrum of a near infrared region. The modified transmission property includes a transmission property with a pass band of the near infrared region.

Effects of the Invention

According to the discrimination filtering device of the present invention, an obtained signal passed through a filter with a first pass band is normalized by an integral of a light intensity from an object obtained through a filter with a second pass band encompassing the first pass band and a discriminant analysis of the object is then performed based on the normalized signal. Thus, a discriminant analysis of an object can be carried out readily by the present invention.

DESCRIPTION OF THE REFERENCE NUMBERS

10 discrimination filtering device; 20 optical system; 20.1 first filter; 20.2 second filter; 30 detection unit; 40 processing unit; 42 storage unit; 50 result output unit; 100 camera; 110 first lens; 120 filter switching unit; 122 shaft; 130 second lens; 140 quick return mirror; 150 CCD; 160 pentaprism; 170 third lens; 180 optical finder; 190 flash; 200 image processing unit; 210 first filter; 220 second filter; 230 beam splitter; 240, 250 image sensing element; 310 lens; 320 memory; 330 display panel; 340 filter support unit; 600 computer; 610 CPU; 620 RAM; 630 hard disk; 640 keyboard; 650 mouse; 660 external interface; 670 monitor; 810 ice; 820 water; 830 asphalt; 840 sensor; 850 near infrared spectroscope; 860 personal computer; 1600 discrimination filtering device; 1610 light receiving element; 1620 filter; 1630 light source; 1640 indicator; 1645 buzzer; 1650 amplifier; 1660 processor; 1690 LED power source; 1700 tube; 1710 round tube; 1720 square tube; 1730 round tube; 2400 discrimination filtering device; 2500 discrimination filtering device; 2510 light receiving element array; 2520 filter array; 2600 discrimination filtering system; 2610 specimen measurement device; 2620 cable.

BEST MODES FOR CARRYING OUT THE INVENTION

First Embodiment

1. Overview

Figure 1:
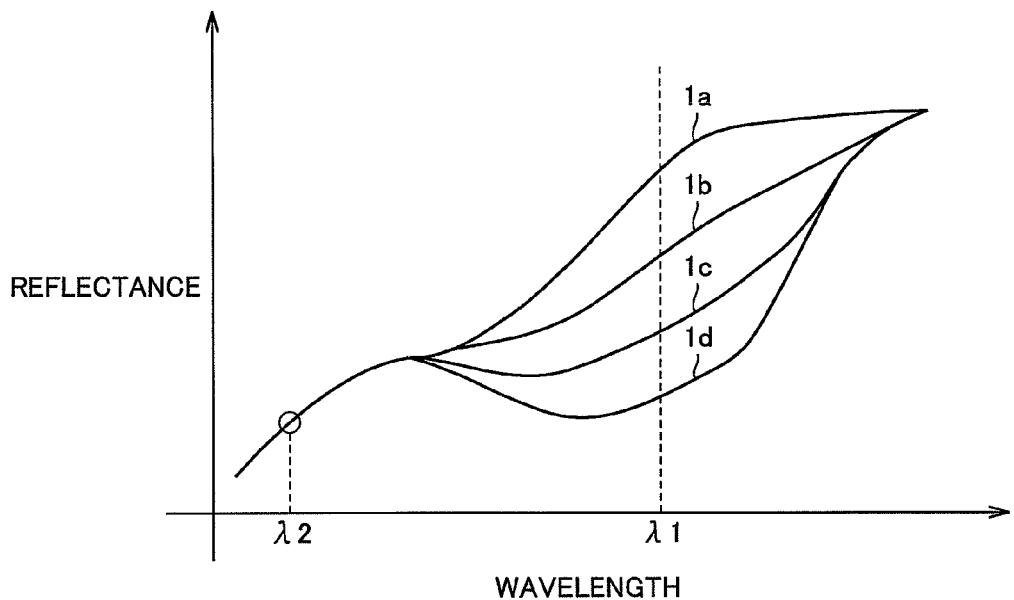
FIG. 1 is a diagram to describe discrimination of a specimen utilizing conventional spectroscopic technique.
Figure 2:
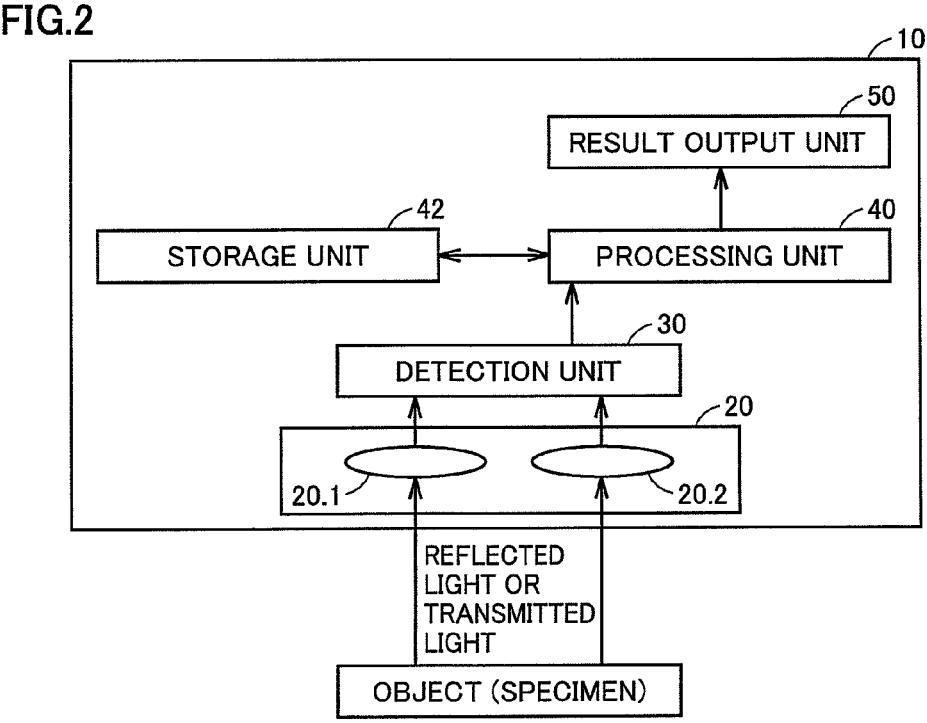
FIG. 2 represents a configuration of a discrimination filtering device in block form according to an embodiment.

A discrimination filtering device 10 according to an embodiment will be described schematically with reference to FIG. 2. FIG. 2 represents the configuration of discrimination filtering device 10 of the present embodiment in block form.

Referring to FIG. 2, discrimination filtering device 10 includes an optical system 20, a detection unit 30, a processing unit 40, a storage unit 42, and a result output unit 50.

Optical system 20 includes a plurality of optical elements. The light from a specimen that is the object of discrimination (light reflected from or passed through the specimen) enters detection unit 30 via optical system 20.

The term "light" used herein refers to, not only visible light, but also general electromagnetic wave employed in discrimination of a specimen. Namely, "light" used herein refers to an electromagnetic wave that interacts with the specimen. Specifically "light" includes visible light, near infrared light, far infrared light, ultraviolet light, and the like.

Particularly, optical system 20 includes a first filter 20.1 and a second filter 20.2. First filter 20.1 has a first pass band. Second filter 20.2 has a second pass band encompassing the first pass band. The first pass band and the second pass band are designed depending on the property of the specimen under discrimination by discrimination filtering device 10. The designing method of filters will be described afterwards.

Optical system 20 also includes optical elements such as a lens and mirror in addition to first and second filters 20.1 and 20.2. Optical elements other than first and second filters 20.1 and 20.2 are dispensable, depending upon the positional relationship between the specimen and detection unit 30.

Detection unit 30 detects an electromagnetic wave output from the specimen and passed through one of first and second filters 20.1 and 20.2. Detection unit 30 outputs a signal corresponding to the intensity of the detected electromagnetic wave. A signal corresponding to the intensity of the electromagnetic wave passed through first filter 20.1 is referred to as "first signal" hereinafter. A signal corresponding to the intensity of the electromagnetic wave passed through second filter 20.2 is referred to as "second signal".

Processing unit 40 conducts discrimination of a specimen based on first and second signals from detection unit 30. Specifically, processing unit 40 performs a discriminant analysis of the specimen based on a first signal normalized by an integral of the second signal. Further details of the processes carried out by processing unit 40 will be described afterwards.

Storage unit 42 stores data. Specifically, storage unit 42 stores a program to be executed by processing unit 40, computed results from processing unit 40, and the like.

Result output unit 50 outputs a discrimination result of a specimen through processing unit 40. For result output unit 50, a monitor displaying a screen indicating the computation result, an indicator emitting light according to the computation result, a buzzer issuing a sound according to the result, or the like may be used, for example. Alternatively, result output unit 50 may be an interface that provides the discrimination result to an external source.

The present embodiment will be described corresponding to the case where discrimination filtering device 10 is a camera.

Figure 3:
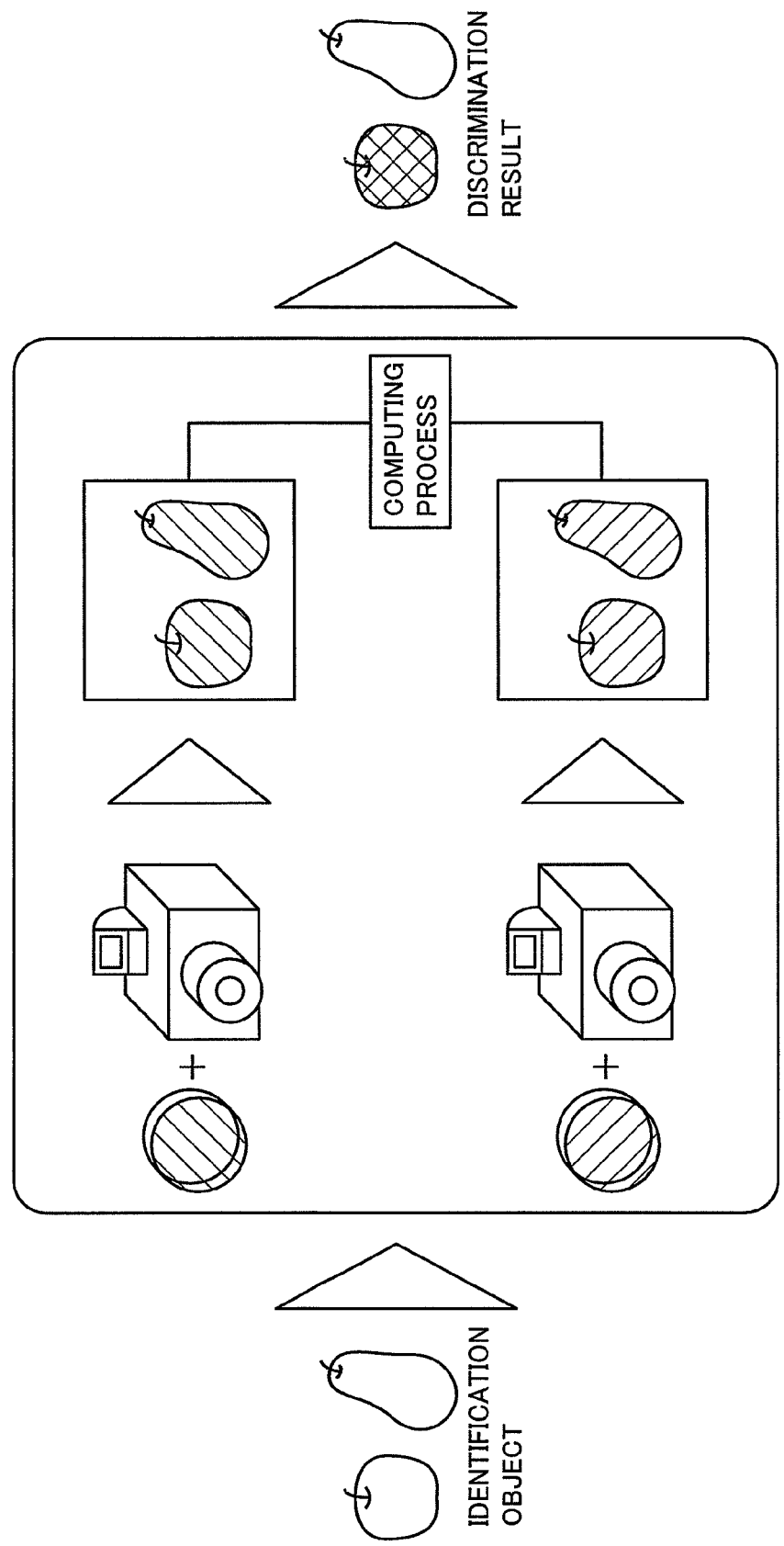
FIG. 3 is a diagram to describe an overview of specimen discrimination according to the embodiment.

An overview of a discriminant analysis according to the present embodiment will be described with reference to FIG. 3. FIG. 3 is a diagram to describe an overview of a discriminant analysis of the present embodiment.

In a discriminant analysis of the present embodiment, an object that is the subject of identification is photographed several times by a camera through spectral filters each having a different pass band. The value of each pixel of the image output from the camera by the image pickup corresponds to the integrated value with regards to the wavelength over each filter pass band in the spectrum.

The pass band of each filter is designed to suit discrimination of an object. The method of designing filters and the feature of the designed filters will be described afterwards.

The object is subjected to discrimination based on the two output images. In the present embodiment, it is assumed that which of the two groups the object belongs to is inferred using a linear discriminant analysis. Specifically, the output result is substituted into the discrimination function determined based on the transmission property of each filter and a teaching spectrum obtained in advance to allow inferring the group which the object belongs to depending upon whether the result of substitution is positive or negative.

2. Camera Configuration

Figure 4A:
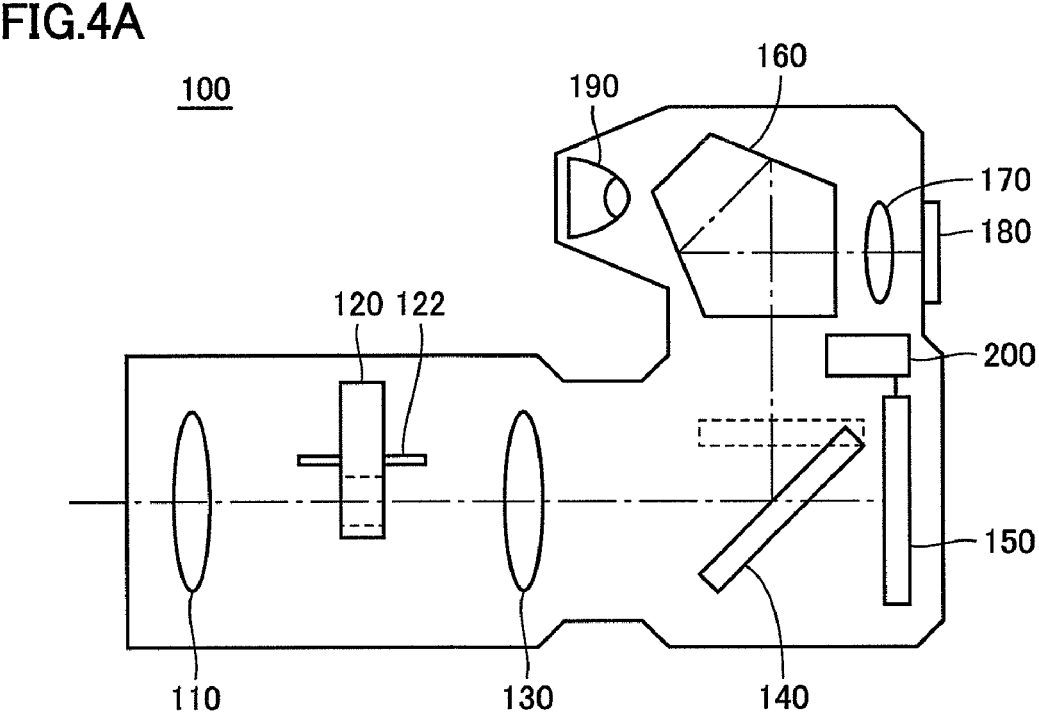
FIG. 4A is a side sectional view of a camera.
Figure 4B:
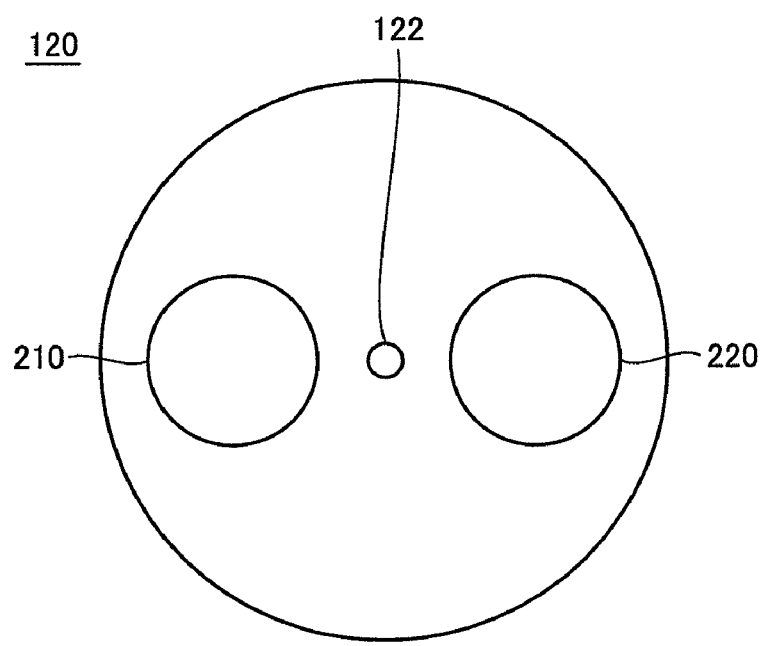
FIG. 4B is a front view of a filter switch unit.

A configuration of camera 100 of the present embodiment will be described with reference to FIGS. 4A and 4B. FIGS. 4A and 4B are diagrams to describe the configuration of camera 100 according to the present embodiment.

FIG. 4A is a sectional side view of camera 100. As shown in FIG. 4A, camera 100 includes a first lens 110 for collecting light from an object that is the image pickup target, a filter switching unit 120, a second lens 130 for adjusting the convergence of the beam of light, a quick return mirror 140, a CCD (charge-coupled device) 150, a pentaprism 160, a third lens 170, an optical finder 180, a flash 190 for producing light on the object, and an image processing unit 200.

FIG. 4B is a front view of filter switching unit 120. Filter switching unit 120 includes a shaft 122, and first and second filters 210 and 220, as shown in FIG. 4B. Filter switching unit 120 is rotatable about shaft 122. The light collected at first lens 110 passes through either first filter 210 or second filter 220.

Quick return mirror 140 is located at the position indicated by the solid line shown in FIG. 4A in a general state, and moves to the position indicated by the dotted line at the time of image pickup. Namely, the light is guided towards optical finder 180 in a general mode, and towards CCD 150 in an image pickup mode.

CCD 150 converts the intensity of the incident light into an image signal, and outputs a value corresponding to an integral of the image signal over a wavelength thereof. CCD 150 is an example of an image sensing element for obtaining information of the light intensity. A configuration employing a CMOS (Complementary Metal Oxide Semiconductor) sensor in lieu of CCD 150 may be employed instead. Alternatively, an Si light receiving element, a group III-V compound semiconductor light receiving element such as of InGaAs, Ex-InGaAs or the like, a group II-IV light receiving element such as of HgCdTe or the like, a thermal infrared sensitive element such as of MEMS or the like may be employed.

The output result from CCD 150 is provided to image processing unit 200. Image processing unit 200 conducts discrimination of the object based on the output results.

Camera 100 shown in FIGS. 4A and 4B obtains the images of an object through the transmission of two types of filters by means of filter switching unit 120. Alternatively, a beam splitter may be employed instead of filter switching unit 120.

Figure 5:
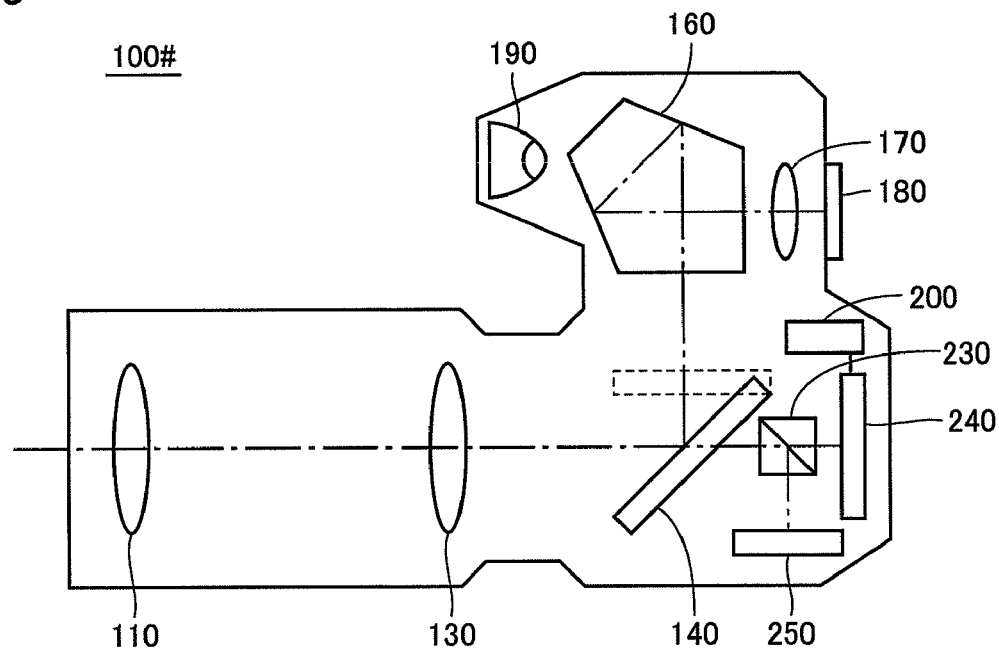
FIG. 5 is a diagram to describe a configuration of a camera according to a modification.

A modification of such a camera is shown in FIG. 5. FIG. 5 is a diagram to describe a configuration of a camera 100# according to the modification.

Camera 100# differs from camera 100 in that a beam splitter 230 is incorporated instead of filter switching unit 120, and that two image sensing elements (image sensing element 240, image sensing element 250) are incorporated. First filter 210 is arranged between beam splitter 230 and image sensing element 240. Second filter 220 is arranged between beam splitter 230 and image sensing element 250.

Beam splitter 230 splits the light in the direction of first filter 210 and in the direction of second filter 220.

Camera 100# is advantageous in that two images can be taken through one procedure, whereas camera 100 is advantageous in that fewer pixels of the image sensing element are required, allowing a compact device.

The configurations of cameras 100 and 100# are not limited to those shown in FIGS. 4 and 5. For example, a configuration having the number of lenses modified, a configuration without quick return mirror 140, pentaprism 160, third lens 170, and optical finder 180, or a configuration without flash 190 may be employed.

Figure 6:
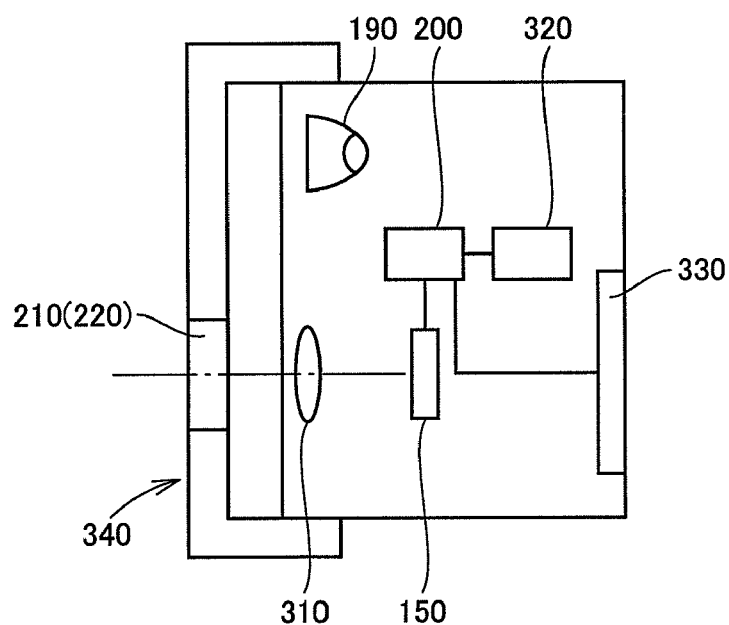
FIG. 6 represents a configuration of a digital camera.

For example, a digital camera 100## of a more simple configuration may be employed instead of camera 100 and camera 100#. FIG. 6 shows a configuration of digital camera 100##.

Digital camera 100## includes a lens 310, a CCD 150, an image processing unit 200, a memory 320, a display panel 330, a flash 190, and a filter support unit 340.

Filter support unit 340 supports first filter 210 or second filter 220. Filter support unit 340 is attached to the casing of digital camera 100##. At the time of attachment to digital camera 100##, filter support unit 340 fixedly supports first filter 210 or second filter 220 such that the light passed through first filter 210 or second filter 220 enters lens 310.

Filter support unit 340 includes a filter switching mechanism described with reference to FIG. 4 to switch the filter located in front of lens 310. Alternatively, a plurality of filter support units 340 each having a different filter attached may be prepared. In this case, the user attaches any one of filter support units 340 to digital camera 100## each time an object of interest is to be photographed.

Lens 310 forms an image on CCD 150 corresponding to the incident light. Image processing unit 200 stores the output result from CCD 150 in memory 320. Image processing unit 200 displays an image based on the output result from CCD 150 on display panel 330.

Alternatively, a camera loaded with the first filter and another camera loaded with the second filter may be used instead of one camera. It is assumed that the performance of such two cameras used is identical. Namely, when the same object is photographed under the same condition when the filter is not mounted, same images will be obtained.

Although a still picture camera was taken as an example here, a motion picture camera may of course be used.

3. Filter Designing Method

Figure 7:
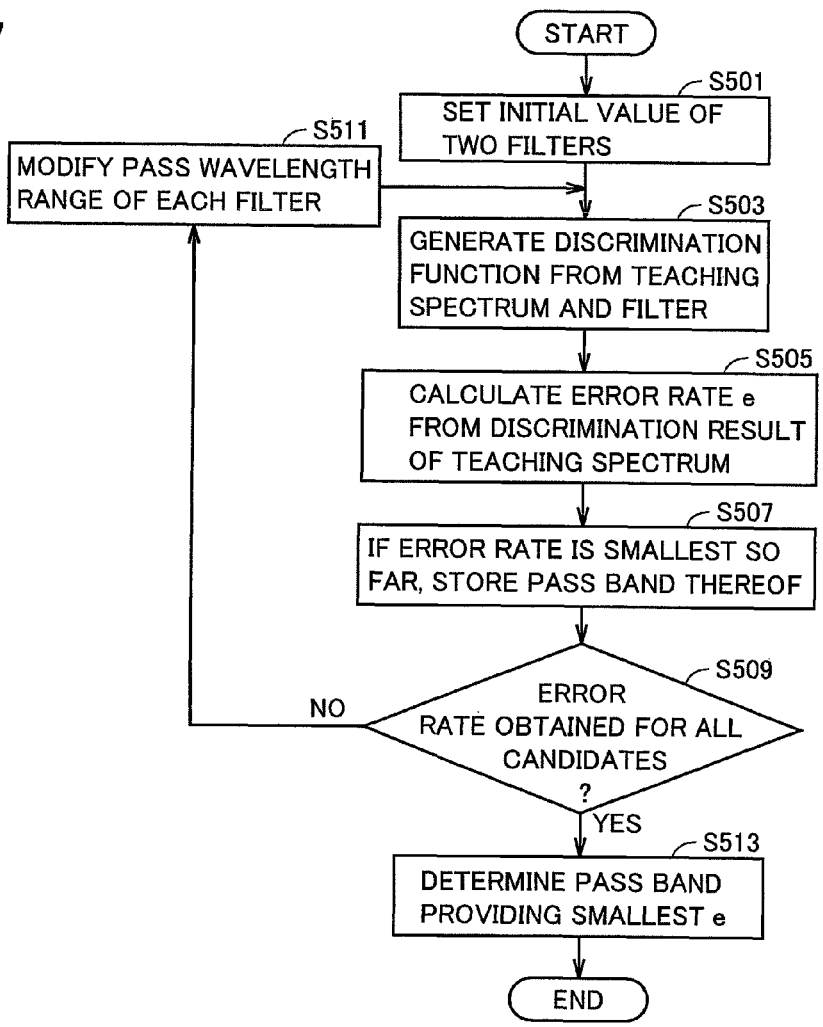
FIG. 7 is a flowchart of the process flow of designing filters according to the embodiment.

A designing method of filters will be described with reference to FIG. 7. FIG. 7 is a flowchart representing the flow of the processes for designing filters according to the present embodiment.

Figure 8:
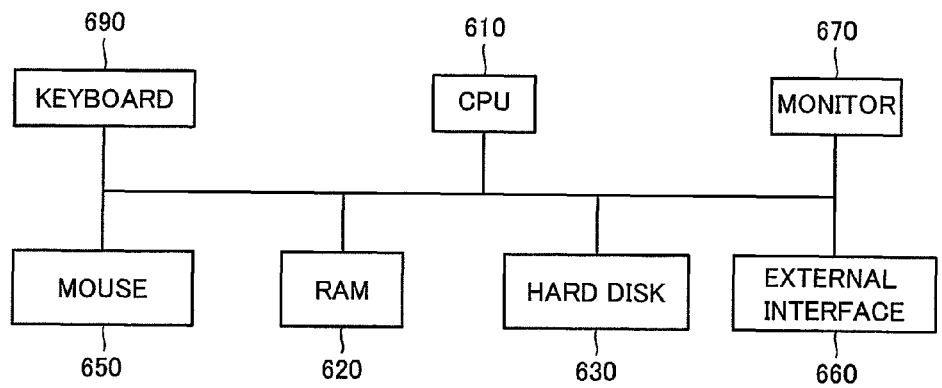
FIG. 8 is a diagram to describe a hardware configuration of a computer.

In the present embodiment, it is assumed that each process in FIG. 7 is implemented by computer 600 as shown in FIG. 8. FIG. 8 is a diagram to describe a hardware configuration of computer 600.

Computer 600 includes a CPU (central processing unit) 610, a RAM (random access memory) 620, a hard disk 630, a keyboard 640, a mouse 650, an external interface 660, and a monitor 670.

CPU 610 executes various processes. RAM 620 stores temporary data and the like generated during execution of a process by CPU 610. Hard disk 630 stores a program directed to designing filters and/or properties of the designed filters. Keyboard 640 and mouse 650 accept an externally applied instruction to send a signal in accordance with the instruction to CPU 610. External interface 660 receives externally applied data such as a spectrum measured by a spectroscope. Monitor 670 displays data and the like stored in hard disk 630.

CPU 610 executes various processes for filter designing as will be described hereinafter by executing a program stored in hard disk 630 on RAM 620.

Although filter designing implemented in software will be described here, filter designing may be realized by hardware such as a dedicated circuit or the like.

At step S501, CPU 610 sets the initial value of the parameters for the transmission properties of the two filters. The initial value may be determined in advance in a program, or may be input through keyboard 640 or the like.

It is assumed that the filter to be designed in the present embodiment is limited to an ideal bandpass filter that thoroughly transmits light from a certain wavelength value to another wavelength value and blocks off light of other wavelength regions. Therefore, the transmission properties of the first filter and second filter can be represented by the pass band alone, as in equation (1) and equation (2).

$$T_1(\lambda)=1(x_1^{(0)} \leq \lambda < y_1^{(0)}, 0 (\text{otherwise})) \quad (1)$$

$$T_2(\lambda)=1(x_1^{(0)} \leq \lambda < y_1^{(0)}, 0 (\text{otherwise})) \quad (2)$$

It is assumed that the value of the longer wavelength side edge and the transmission width are taken as the parameters representing the filter transmission property. Alternatively, the filter transmission properties may be represented by parameters other than the value of the longer wavelength side edge and transmission width. Moreover, the configuration of the filter to be designed is not limited to a bandpass filter, and designing of other types of filters may be employed.

At step S503, CPU 610 generates a discrimination function from the teaching spectrum stored in hard disk 630 and the set transmission property.

As used herein, a teaching spectrum refers to a spectrum of a sample having the group that it belongs to identified in advance (hereinafter, referred to as teaching sample). Teaching spectra are prepared for a plurality of samples. In order to improve the discrimination accuracy, it is preferable to prepare many teaching spectra. It is assumed that each teaching sample belongs to either group a or group b in the present embodiment.

Discrimination function $f(\cdot)$ is a function to infer which of the two groups the sample represented by a set of a plurality of variables belongs to. When a set "A" of variables (though represented by a single character, it means a vector with a number of elements identical in number to the variables) characterizing a sample is given, which of the groups the applied sample belongs to is inferred based on whether $f(A)$ takes a positive value or a negative value. In the present embodiment, $A=(\log R_1, \log R_2)'$ is employed as a variable, where "'" represents transposition of a matrix. $R_i(i=1,2)$ is the output value of the image sensing element corresponding to the passage through the filter of a set transmittance property $T_i(\lambda)$, given by the following equation (3) where $S(\lambda)$ is the spectrum of the sample.

$$R_i = \int T_i(\lambda) S(\lambda) d\lambda \quad (3)$$

Strictly, the characteristics of the image sensing element itself must be taken into account in obtaining $R_i$. Since the characteristics of the image sensing element can be included in the formula of $T_i(\lambda)$, the method disclosed herein allows the inclusion of the characteristics of the image sensing element itself.

Discrimination function f(A) is given by the following equation (4) using each of the average $\mu_a$ and the average $\mu_b$ (a vector likewise with A) of a variable set A of a teaching sample belonging to a relevant group (in order to distinguish from the general A, the variable set of the teaching sample is represented as A*).

$$f(A)=(\mu_a-\mu_b)'\Sigma^{-1}(A-(\mu_a+\mu_b)/2) \quad (4)$$

where $\Sigma$ is the variance-covariance matrix of the group. It is assumed that the variance-covariance is equal between both groups and that the existing ratio in the parent population is equal between both groups.

The discrimination function can be rewritten as equation (5) set forth below using $P=\Sigma^{-1}(\mu_a-\mu_b)$.

$$f(A) = P'A + P'((\mu_a + \mu_b)/2) \quad (5)$$
$$= P_1 \log R_1 + P_2 \log R_2 + P'((\mu_a + \mu_b)/2)$$

In other words, the discrimination function can be described as a linear conversion on the camera output. As appreciated from the equation, P is a factor involved with the camera output.

At step S505, CPU 610 discriminates each teaching spectrum using the discrimination function generated at step S503, and the error rate e of that discrimination is calculated. Error rate e is given by the following equation (6)

$$e = p(f(A^*) < 0 \mid a) \times N_a/(N_a + N_b) + p(f(A^*) < 0 \mid b) \times N_b(N_a + N_b) \quad (6)$$

where $N_a$ and $N_b$ are the number of teaching samples belonging to group a and group b, respectively, $p(f(A^*)<0|a)$ is the probability of the teaching sample belonging to group a being classified as group b, and $p(f(A^*)<0|b)$ is the probability of the teaching sample belonging to group b being classified as group a.

Figure 9:
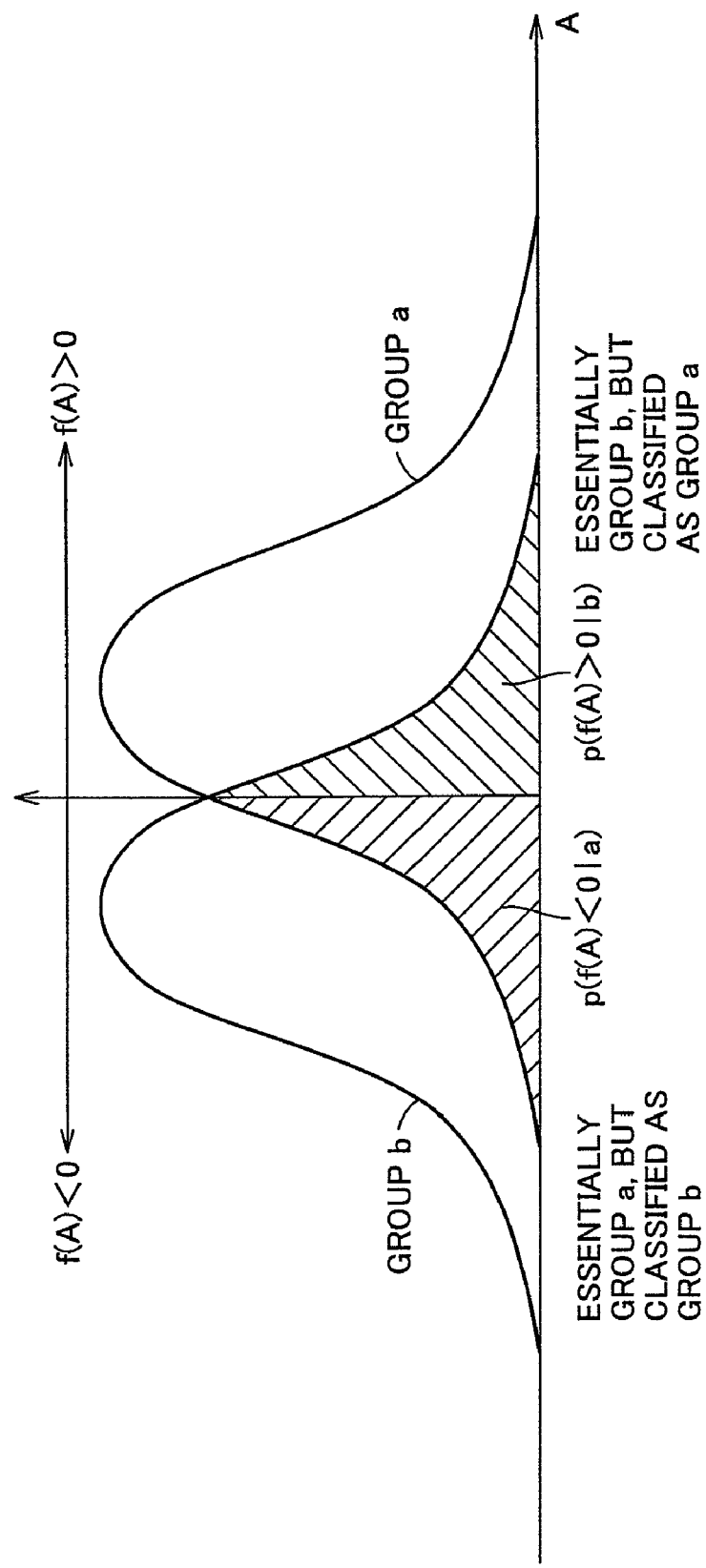
FIG. 9 is a diagram to describe an error rate e.

The meaning of equation (6) will be clarified with reference to FIG. 9. FIG. 9 is a diagram to describe error rate e. In FIG. 9, the horizontal axis represents A (essentially, a vector with two elements, but represented uniaxially for the sake of simplification), and the vertical axis represents the number of samples.

As shown in FIG. 9, the teaching samples of each group are distributed over a constant width about the average value of each group. Therefore, there are some teaching samples belonging to group a but classified as group b because of the result of f(A)<0 and/or teaching samples belonging to group b but classified as group a because of the result of f(A)>0. This lead to erroneous discrimination.

Although FIG. 9 corresponds to the case where the number of samples is identical between group a and group b with the same manner of distribution, there may cases whether the number of samples differ. $N_a/(N_a+N_b)$ and $N_b/(N_a+N_b)$ in equation (5) are weighting factors taking into account the number of samples.

At step S507, CPU 610 stores the set pass band if error rate e is the smallest so far.

At step S509, CPU 610 determines whether the error rate has been obtained for all the predetermined candidate pass bands.

In the case where the error rate for all the candidates has not yet been obtained (NO at step S509), CPU 610 alters the filter pass wavelength range at step S511, and repeats the process from step S503 to step S509.

When the error rate has been obtained for all the candidates (YES at step S509), CPU 610 extracts the pass band that provides the smallest e at step S513. Namely, the pass band stored at step S507 is extracted as the pass band providing the smallest e.

The way to determine a pass band is not limited to the above-described round-robin scheme. An algorithm for determining a candidate with the smallest error rate may be employed instead of the round-robin scheme. By way of example, simulated annealing (for example, refer to S. Kirkpatrick, C. D. Gelatt, Jr., M. P. Vecchi, "Optimization by Simulated Annealing", SCIENCE, Vol. 220, No. 4598, pp. 671-680, 1983) or genetic algorithm (for example, refer to "Neighborhood Cultivation Genetic Algorithm for Multi-Objective Optimization Problems" by Shinya Watanabe, Tomoyuki Hiroyasu, and Mitsunori Miki, Information Processing Society of Japan, Vol. 43, pp. 183-198, 2002; "Genetic Algorithm and Genetic Programming" by Hiromi Hirano, Personal Media Co., Ltd., 2000; "Trade-off Analysis Method" by Tadashi Kuroiwa, Toshiba Review, Vol. 60, No. 1, pp. 48-51, 2005; and the like) may be employed.

4. Example 1

A specific example of filters designed by the filter designing method set forth above, and specimen discrimination results employing the designed filters will be described hereinafter.

Figure 10:
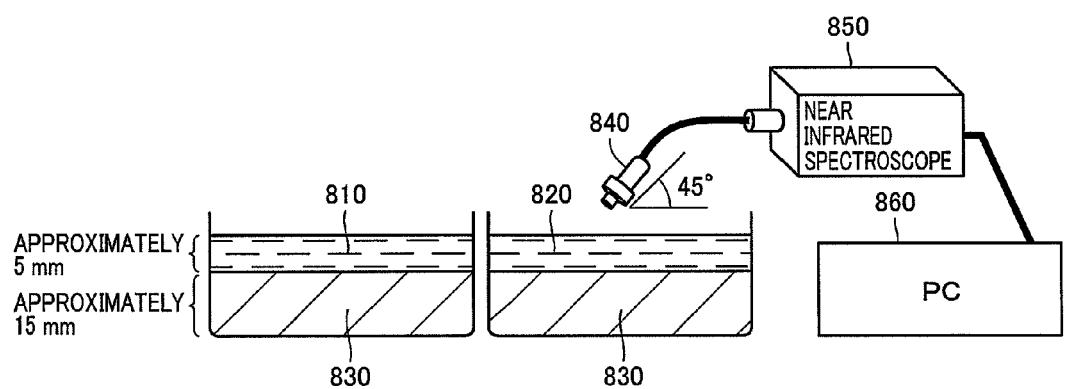
FIG. 10 is a diagram to describe an overview of obtaining a teaching spectrum.

In designing filters, the spectrum (teaching spectrum) for a plurality of types of specimens whose classification is identified in advance must be obtained. An overview of obtaining a teaching spectrum will be described with reference to FIG. 10. FIG. 10 is a diagram to describe an overview of obtaining a teaching spectrum.

In the present example, ice 810 (hereinafter, also referred to as "frozen state") on asphalt 830, and water 820 (hereinafter, also referred to as "wet state") on asphalt 830 were prepared as specimens. The thickness of asphalt 830 was approximately 15 mm. The thickness of ice 810 and water 820 was approximately 5 mm.

These specimens were measured using a sensor 840 to obtain a teaching spectrum by a near infrared spectroscope 850. In the present example, 72 spectra were taken, measured from 920 nm to 1060 nm in the steps of 10 nm for each of ice 810 and water 820.

In detail, a spectrum at each wavelength was measured at the grid points of 8 (vertical)×9 (lateral) of ice 810 or water 820 in a certain range. Thus, the spectra measured at different points have variation due to the influence of the environment. By obtaining teaching spectra with variation, a filter that allows appropriate specimen discrimination even under various environments can be designed.

Figure 11:
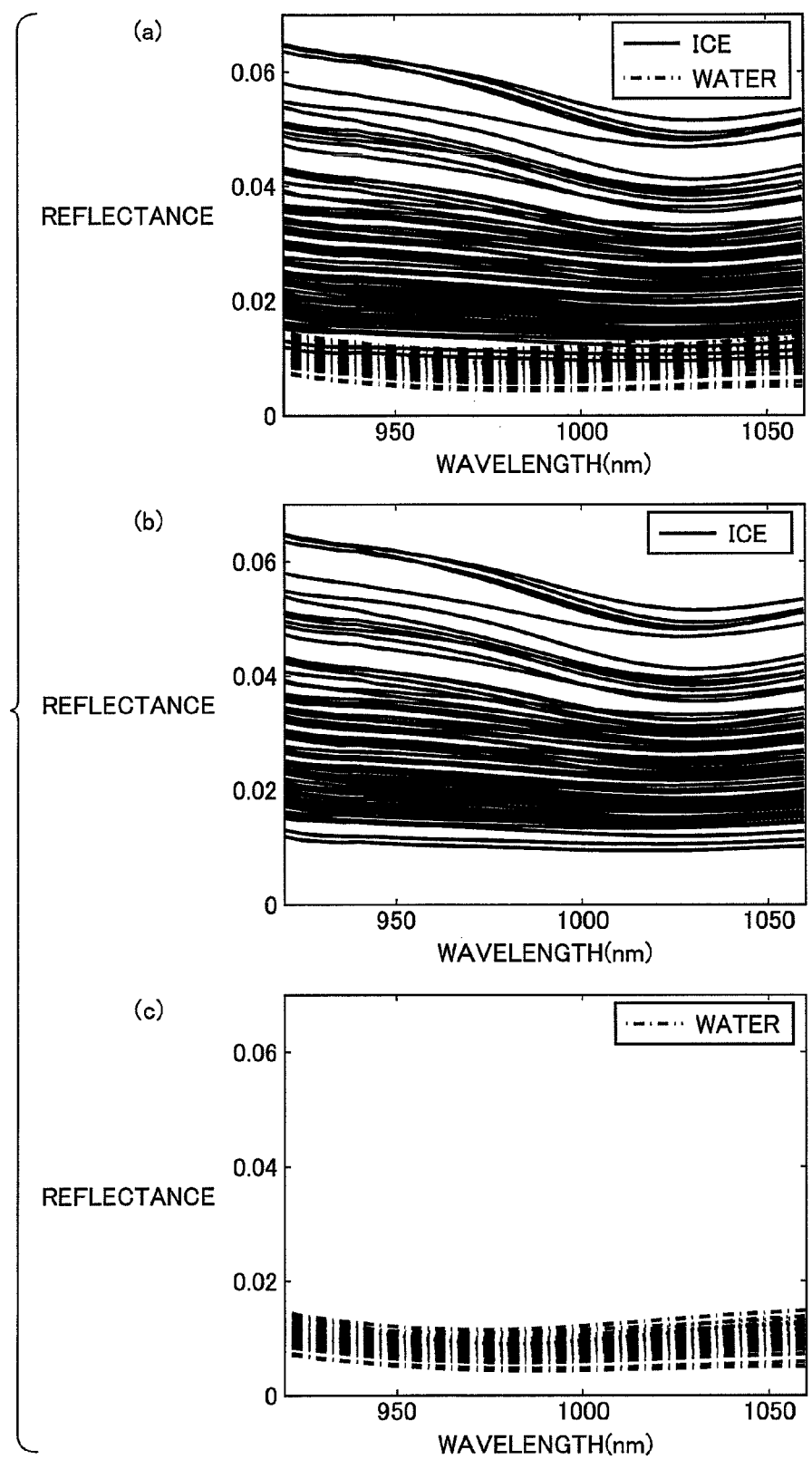
FIG. 11 represents teaching spectra according to Example 1.

The obtained teaching spectra are shown in FIG. 11. In FIG. 11, (a) represents the spectra of both ice and water, (b) represents the spectra of ice alone, and (c) represents the spectra of water alone. In each diagram, the horizontal axis represents the wavelength, and the vertical axis represents the reflectance.

As appreciated from FIG. 11(a), the spectra for both ice and water have a wider range in reflectance. This spread is mainly due to variation in the measurement environment. The spectra of ice are not completely separated from the spectra of water due to this spread.

Measurement of a teaching spectrum is preferably carried out under an environment similar to that of photographing the specimen with a spectral filtering camera. This is to reflect the variation caused by the measurement environment appropriately in discrimination.

Near infrared spectroscope 850 outputs the teaching spectrum to personal computer 860. Based on the output teaching spectrum, personal computer 860 calculates the filter property suitable for discrimination of two specimens according to the procedure set forth above. Computer 600 shown in FIG. 8, for example, may be employed for personal computer 860. Personal computer 860 is only a way of example of a processor device that performs filter designing, and a filter may be designed using another device.

Figure 12:
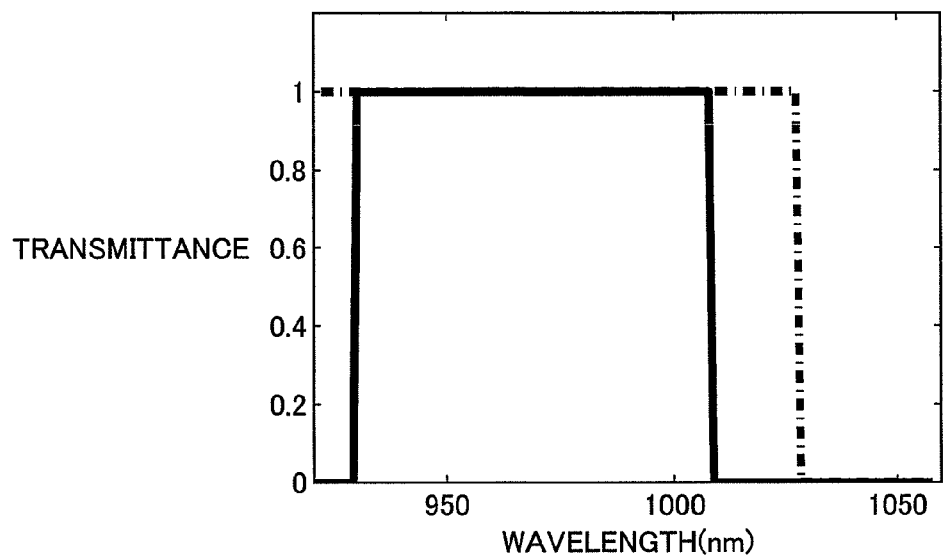
FIG. 12 represents a transmission property of filters designed according to Example 1.

Calculation results will be described with reference to FIG. 12. FIG. 12 represents transmission properties of filters designed in Example 1. A filter allowing the passage of light at 925 nm to 1005 nm (indicated in a solid line) and a filter allowing the passage of light at 920 nm to 1025 nm (indicted by a chain dotted line) were designed.

The coefficient of the discrimination function in the event of using these filters were calculated as $P_1=1.7375$, $P_2=-1.7374$. In this case, the theoretical error rate is 0%.

Figure 13:
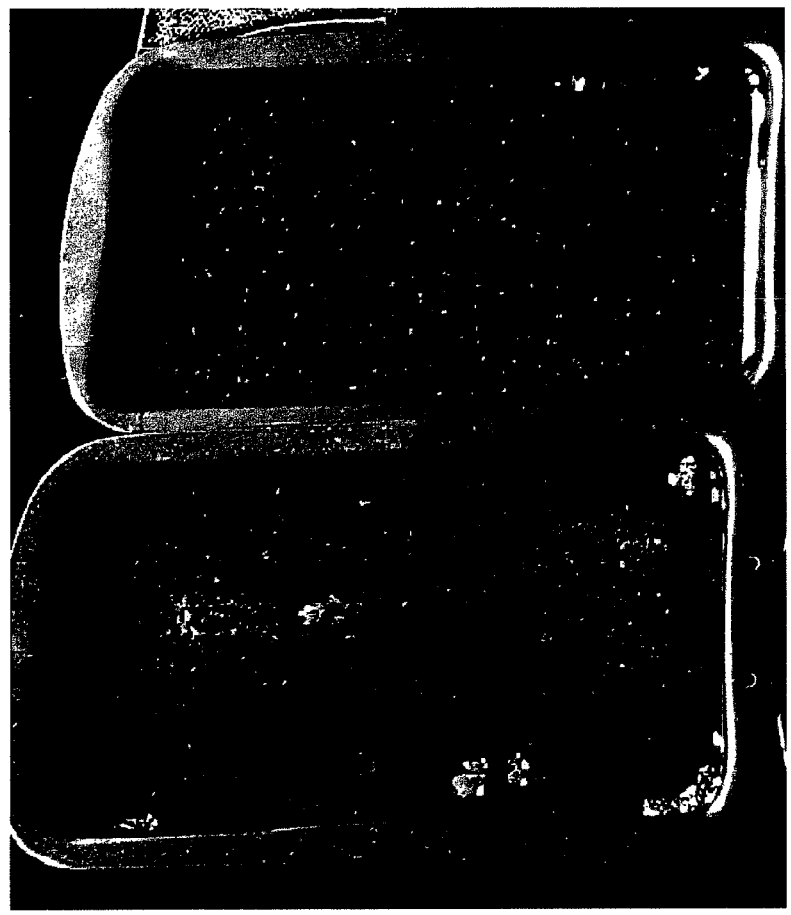
FIG. 13 is an original image of specimens that are the object of discrimination.
Figure 14:
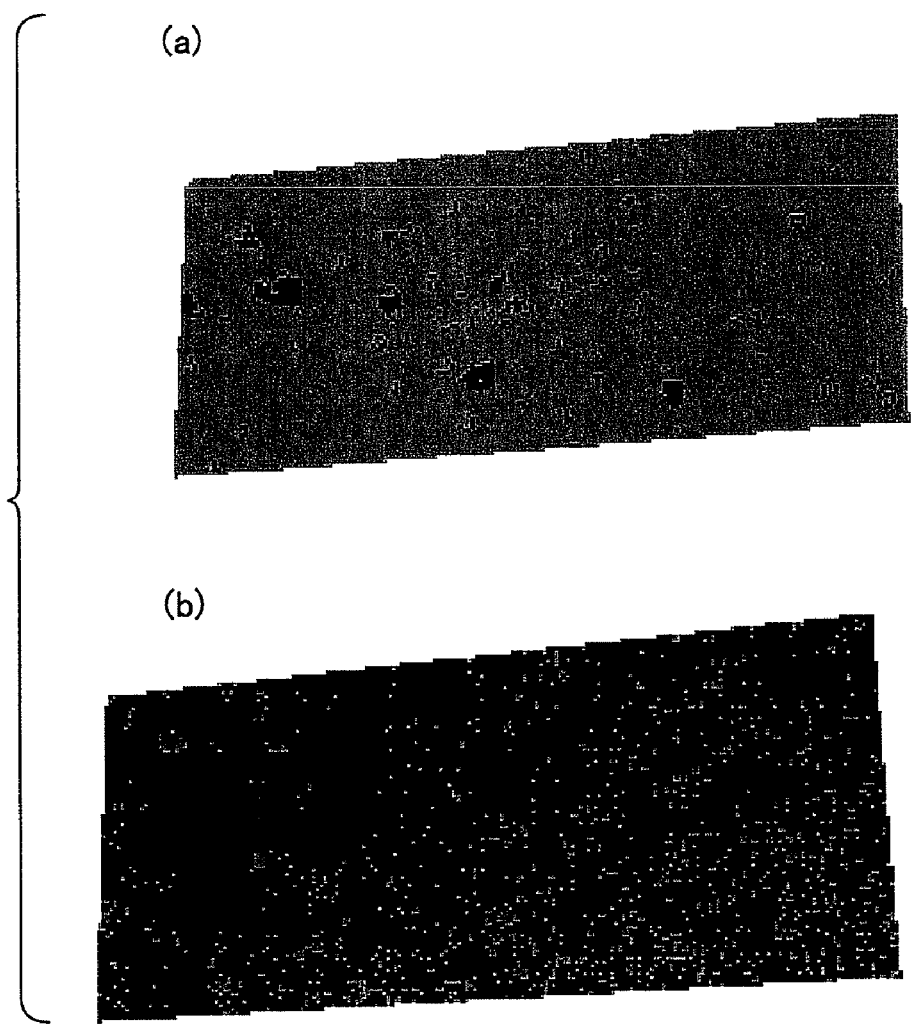
FIG. 14 represents the discrimination results of the specimens shown in FIG. 13.

The discrimination results of specimens using these filters will be described with reference to FIGS. 13 and 14. FIG. 13 represents an original image of specimens that are the target of discrimination. The upper represents a specimen in a wet state, and the lower represents a specimen in a frozen state. FIG. 14 represents the discrimination results of the specimens shown in FIG. 13. In FIG. 14, (a) represents the discrimination result of the specimen in a wet state, and (b) represents the discrimination result of the specimen in a frozen state. In FIG. 14, a pixel based on a determination of a frozen state is represented in black, and a pixel based on a determination of a wet state is represented in gray. The percentage of correct decisions in discrimination was 93.8%.

The designed filters are characterized in that the pass band of one filter is encompassed in the pass band of the other filter. The reason why discrimination of a specimen is preformed appropriately by using such a set of filters is because the filter of the wider pass band functions as a normalization filter to remove the effect of disturbance factors, and the filter of the narrower pass band functions as an identification filter that allows passage of a wavelength of the object of identification separated at higher accuracy.

It can be assumed that the calculated discrimination function corresponds to a simple difference between the logarithm of the output through one filter and the logarithm of the output through the other filter ($P_1$ and $-P_2$ are substantially equal), and the output of one filter is normalized by the output of the other filter using the discrimination function. Since the logarithms of the outputs are compared, normalization is realized by a simple process of taking the difference.

5. Second Example

The above example was described based on designing filters using a spectrum at 920 nm to 1060 nm. The wavelength region of the spectrum to be employed is not limited thereto. Here, designing filters using a spectrum including a longer wavelength region will be described. The discrimination accuracy can be improved by designing filters using a spectrum of a wider wavelength region.

In the present example, 72 spectra at 900 nm to 1695 nm in the steps of 5 nm were measured for each of a frozen state and wet state to be used as the teaching spectrum.

Figure 15:
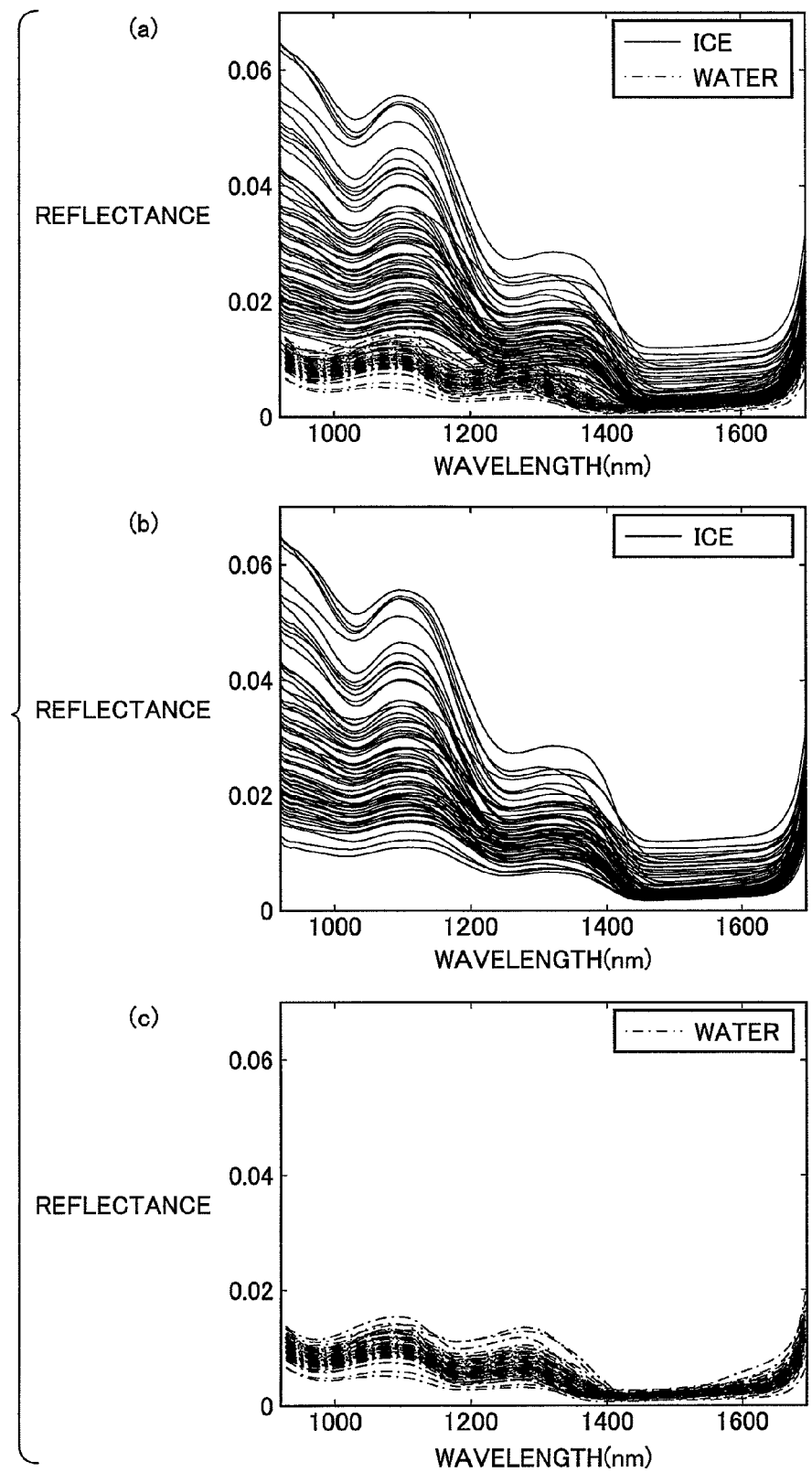
FIG. 15 represents teaching spectra according to Example 2.
Figure 16:
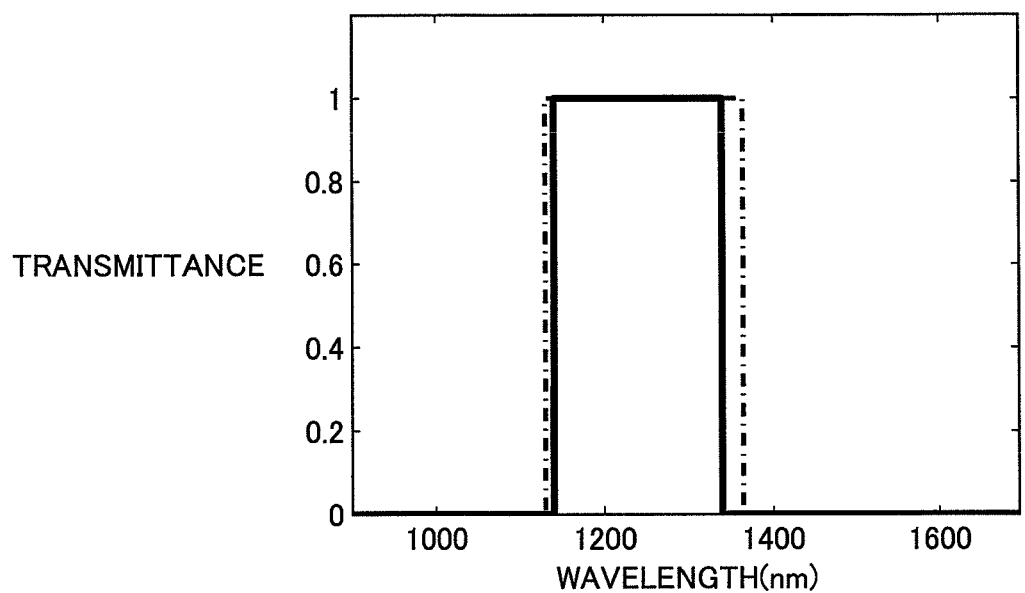
FIG. 16 represents a transmission property of filters designed according to Example 2.

The teaching spectra obtained by the measurements are shown in FIG. 15. In FIG. 15, (a) represents the spectra of both ice and water, (b) represents the spectra of ice alone, and (c) represents the spectra of water alone. In each diagram, the horizontal axis represents the wavelength, and the vertical axis represents the reflectance The transmission property of filters designed based on such teaching spectrum is shown in FIG. 16. A filter allowing the passage of light at 1140 nm to 1335 nm (indicated in a solid line, discrimination filter) and a filter allowing the passage of light at 1130 nm to 1360 nm (indicted by a chain dotted line) were designed.

The coefficient of the discrimination function when these filters are used was calculated as $P_1=-2997.9$, $P_2=3006.8$. In this case, the theoretical error rate is 0%.

Figure 17:
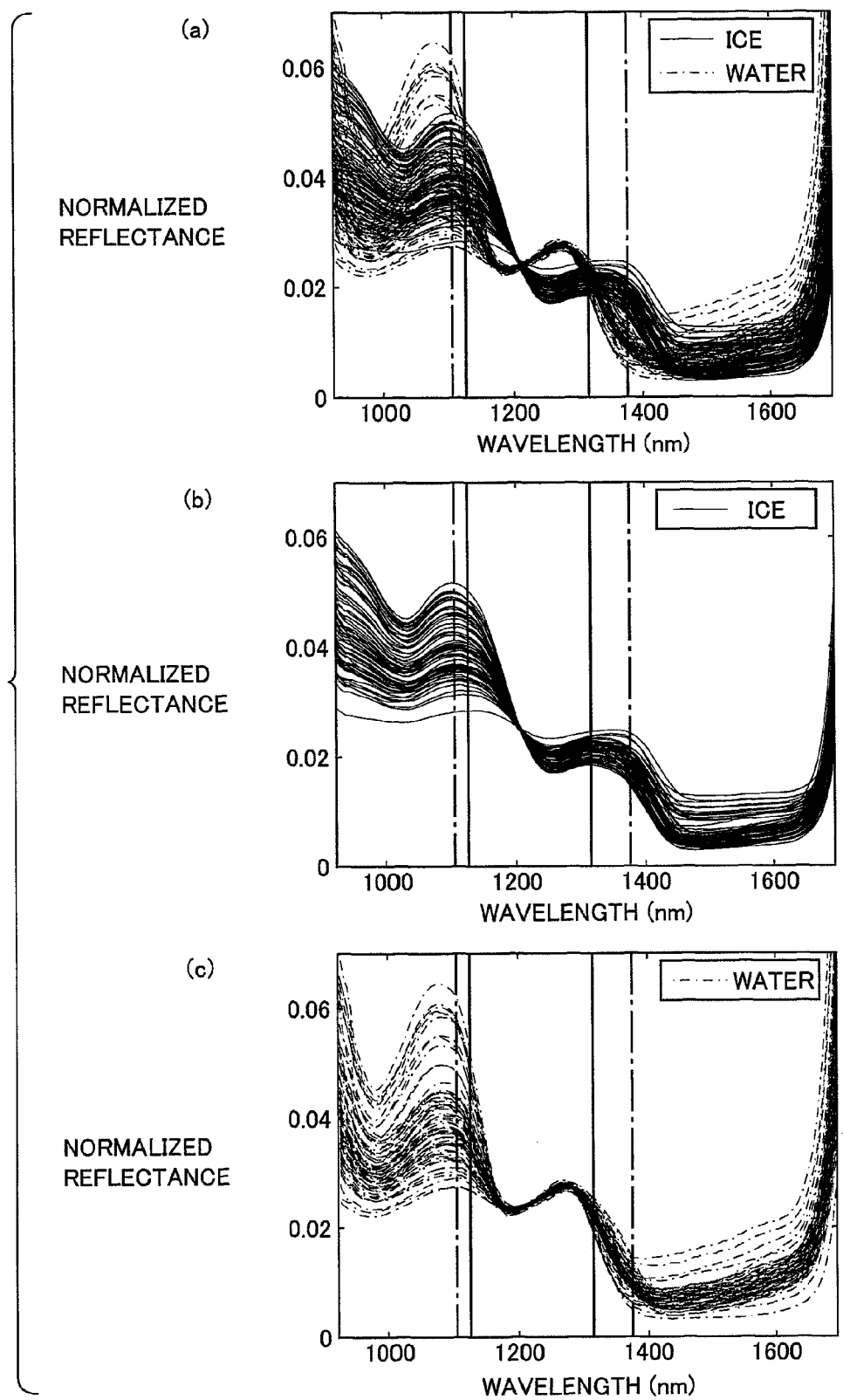
FIG. 17 is a diagram to describe the meaning of the designed filters.

It is appreciated from FIG. 15(a) that discrimination between water and ice is not easy due to the overlapping between the water spectrum and ice spectrum. However, discrimination therebetween is allowed by using the above-described filters. This will be described hereinafter with reference to FIG. 17. FIG. 17 is a diagram to describe the significance of the designed filters.

In FIG. 17, (a), (b) and (c) represent the normalized spectra of water and ice, the normalized spectra of ice, and the normalized spectra of water, respectively. As used herein, "normalization" refers to the process of dividing each spectrum by the output from the camera when photographed through a normalization filter. In FIG. 17, the edge of the normalization filter is represented by a chain dotted line whereas the edge of the identification filter indicated by a solid line.

As shown in FIG. 17(a), the spectra of ice and the spectra of water are clearly separated in the region where the identification filter passes light. In other words, it is appreciated that the identification filter has a pass band suitable for discrimination of a specimen. Specifically, when two specimens are measured under the same environment, the spectra of the two specimens at the pass band of the identification filter have a shape that is readily distinguishable by a predetermined discrimination method. From these results, it is preferable to use a near infrared region of the longer wavelength side for the discrimination of water from ice. Since water has a more abrupt absorption spectrum region in the vicinity of 1.9 micron, it may be desirable to use a pass band in the vicinity thereof for discrimination depending upon the material.

This will be described in line with the discrimination function. Score f(A) of the discrimination function has the constant term removed, and the coefficients of $P_1$, $P_2$ normalized to 1 on the assumption that they are at the same level, giving $f(A)=-\log R_1+\log R_2=\log(R_2/R_1)$. By substituting the formulas of $R_1$ and $R_2$ into the equation, $f(A)=\log(\int T_2(\lambda)S(\lambda)d\lambda/\int T_1(\lambda) S(\lambda) d\lambda)=\log(\int T_2(\lambda)S_n(\lambda)d\lambda)$ is obtained, where $S_n(\lambda)$ is the normalized spectrum. In other words, the logarithm of the integration of the normalized spectrum over the pass band of the identification filter becomes the score of the discrimination function with the constant value removed. Therefore, it can be appreciated that discrimination can be performed appropriately based on the two designed filters and the calculated discrimination function.

According to the method of designing filters according to the present embodiment, two filters suitable for discrimination, i.e. an identification filter having a pass band suitable for discrimination of a specimen, and a normalization filter directed to removing disturbance effects, can be designed.

6. Miscellaneous; Modification of First Embodiment

A discrimination filtering camera according to the present embodiment can also evaluate the moisture content at the surface of or inside a substance based on measurement results.

Although the foregoing description is based on discrimination between water and ice, designing of filters based on a similar method for other specimens, and discrimination of specimens using the designed filters can be carried out.

The discrimination filtering camera may be directed to identifying a substance through images. Namely, the discrimination result may be displayed as an image in a comprehensible manner. For example, image processing unit 200 causes different substances to be displayed in different colors, as in the results shown in FIG. 14.

The number of filters to be designed by the above-described designing method is not limited to two. The designing method set forth above may be expanded to allow the designing of three or more filters. Naturally, a spectral filtering camera employing three or more designed filters can be produced.

Moreover, discrimination of three or more types of specimens can be performed by expanding the method set forth above. In this case, the number of filters should be increased appropriately according to the type of the substance to be discriminated. For the discriminant analysis method, a canonical discriminant analysis or the like may be employed.

The above embodiment was described in which one camera 100 basically includes all the components to perform discrimination of an object. However, it is apparent that, by applying the description set forth above, the discrimination filtering device may be implemented by a system based on a combination of a plurality of devices instead of just one camera 100.

For example, as mentioned already, two different cameras may include a first filter 20.1 and a second filter 20.2, respectively. Alternatively, first filter 20.1 and second filter 20.2 may not be incorporated in a camera. These filters may be prepared separately from the camera.

Alternatively, the discrimination filtering device may be implemented by a camera and a computer. The computer includes an interface to receive the results of an image picked up by the camera, a CPU, and a monitor. In this case, the CPU functions as a processing unit 40, and the monitor functions as a result output unit 50.

In the present embodiment, the discrimination filtering device conducts discrimination of a specimen based on the detected results of light reflected from the specimen. The light incident to the discrimination filtering device is not limited to reflected light, as long as the property of the specimen stands out. For example, the discrimination filtering device may detect the light transmitted through the specimen, and conduct discrimination of the specimen based on the detected result.

The present embodiment was described in which an object was discriminated based on the image pickup result of an object through a camera. Therefore, the discrimination result of an object for each point in an image can be obtained in the present embodiment. As apparent from the fact that an object can be discriminated at each point in an image, the discrimination filtering device can conduct discrimination of an object based on the light detection result of one light receiving element that converts incident light into an electric signal. The discrimination filtering device requires at least one light receiving element.

Second Embodiment

1. Overview

The second embodiment is based on a discrimination filtering device employing a point sensor. The discrimination filtering device of the second embodiment includes a light source. The discrimination filtering device of the second embodiment performs object discrimination utilizing light output from a light source and passed through the object. The discrimination filtering device of the second embodiment can be used for the inspection of a specimen through which light can pass, particularly the inspection of a fluid such as liquid.

Figure 18:
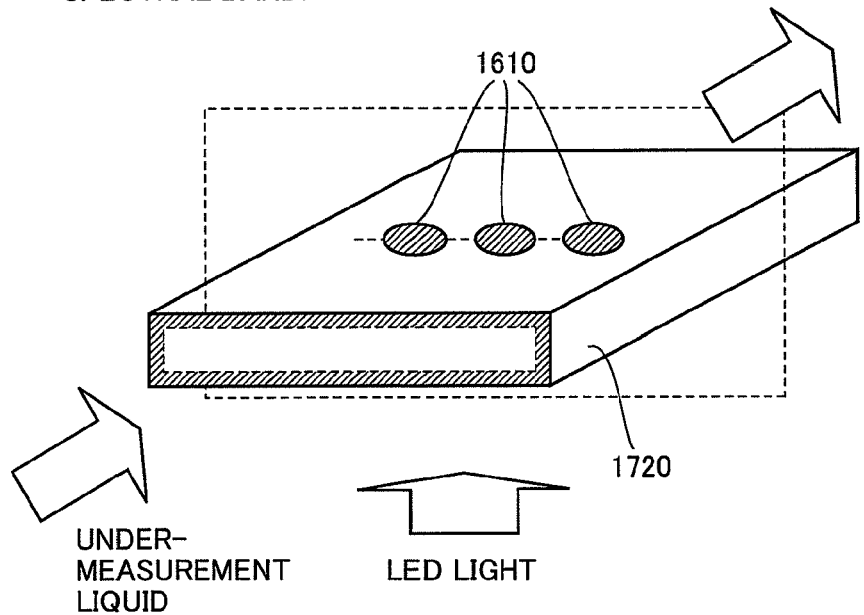
FIG. 18 shows an example of a manner of specimen discrimination according to a second embodiment.

An example of embodying specimen discrimination utilizing the discrimination filtering device according to the second embodiment will be described with reference to FIG. 18. FIG. 18 shows an example of a manner of specimen discrimination according to the second embodiment.

The discrimination filtering device includes an LED light source, a plurality of light receiving elements 1610, and a plurality of filters. The filters are designed by a method similar to that of the first embodiment. A light receiving element 1610 and a filter are arranged in a pair. However, for the sake of simplifying the illustration, a specific configuration of a discrimination filtering device is not shown in FIG. 18. A specific configuration of the discrimination filtering device will be described afterwards with reference to another drawing.

In the present embodiment, the discrimination filtering device analyzes the components included in a liquid flowing through a square tube 1720. The user of the discrimination filtering device of interest arranges the discrimination filtering device so as to surround square tube 1720. Square tube 1720 allows the passage of a liquid to be inspected by the discrimination filtering device. The liquid flows through square tube 1720. In FIG. 18, the direction of flow of the liquid is indicated by an arrow.

Each light receiving element 1610 detects the LED light output from an LED light source and transmitted through the liquid and any one of the filters. The discrimination filtering device performs componential analysis of the specimen (liquid) based on the light detection result of each light receiving element 1610. The discrimination filtering device can analyze the components of the liquid flowing through the region between the LED light source and the light receiving element, as needed.

For the purpose of such a componential analysis of the specimen, the tube through which a specimen passes is preferably a rectangle instead of a circle. This is because the light transmittance of square tube 1720 does not vary substantially from site to site.

Square tube 1720 and the discrimination filtering device preferably disallows the entrance of light from an external source (light other than the LED light). This is for the sake of improving the detection accuracy. For example, the user of the discrimination filtering device should cover square tube 1720 and the discrimination filtering device with a light-blocking material (for example, black box, black cloth, or the like) during specimen analysis. Alternatively, the user may seal square tube 1720 and the discrimination filtering device with black resin. Alternatively, the user may carry out the specimen analysis in a dark room.

The discrimination filtering device of the present embodiment performs specimen discrimination utilizing the light from the light source. Therefore, by covering the filtering device as set forth above, the influence of ambient light can be reduced. By using the discrimination filtering device according to the present embodiment, the discrimination accuracy of a specimen can be improved.

Figure 19:
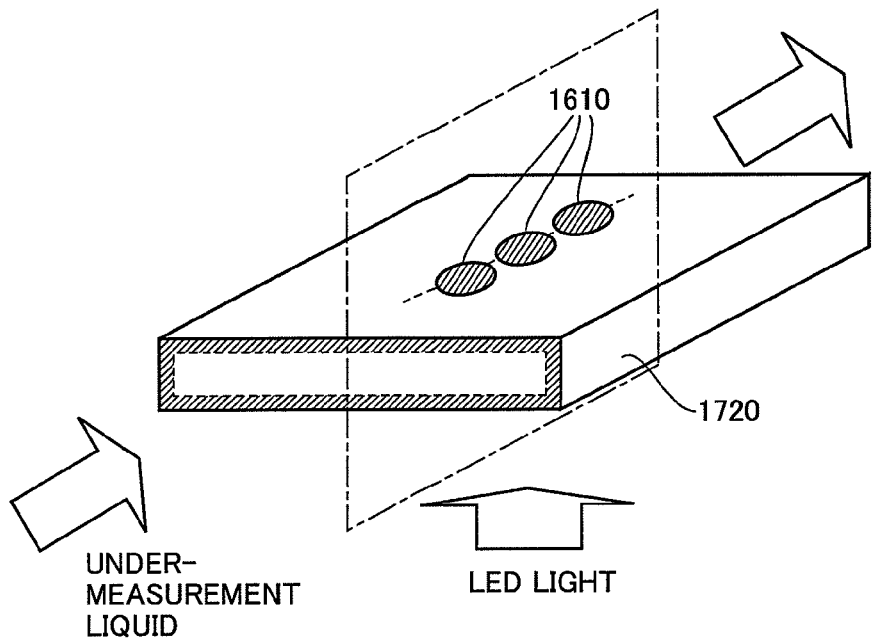
FIG. 19 represents another example of a manner of specimen discrimination according to the second embodiment.

FIG. 18 shows a plurality of light receiving elements 1610 aligned in a one-dimensional manner perpendicular to the flow of the liquid. However, the arrangement of light receiving elements 1610 is not limited to that shown in FIG. 18. For example, a plurality of light receiving elements may be aligned one-dimensionally so as to be orthogonal to the liquid flow, as shown in FIG. 19. FIG. 19 represents another example of a manner of specimen discrimination according to the second embodiment.

More generally, light receiving elements 1610 are to be arranged to allow detection of the LED light transmitted through the object of interest. For example, light receiving elements 1610 may be arranged in a two-dimensional manner instead of along one line.

2. Device Configuration

Figure 20A:
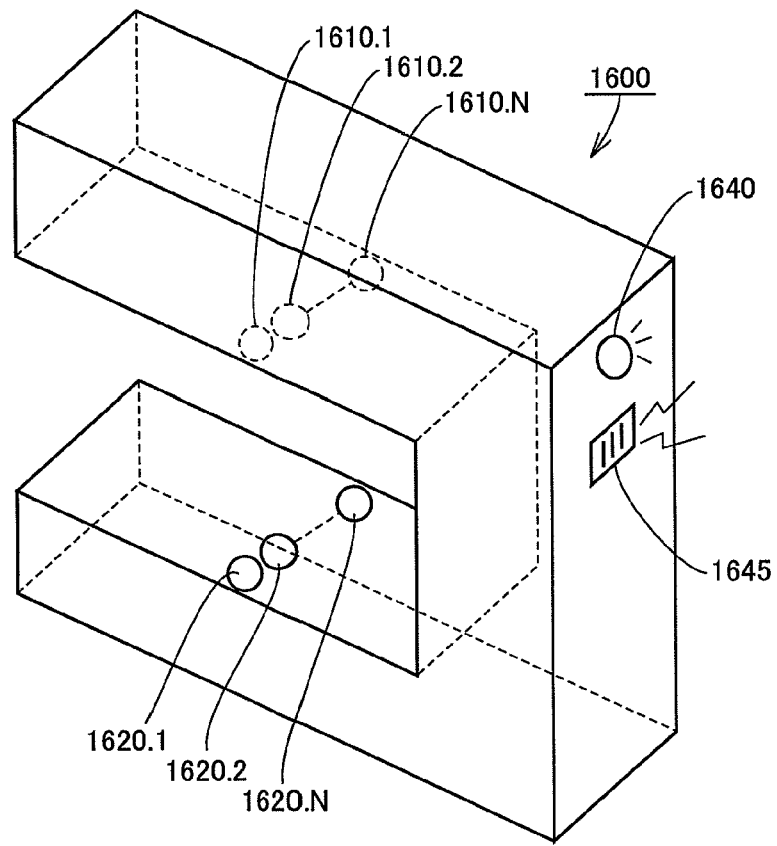
FIG. 20A represents an appearance of a discrimination filtering device.
Figure 20B:
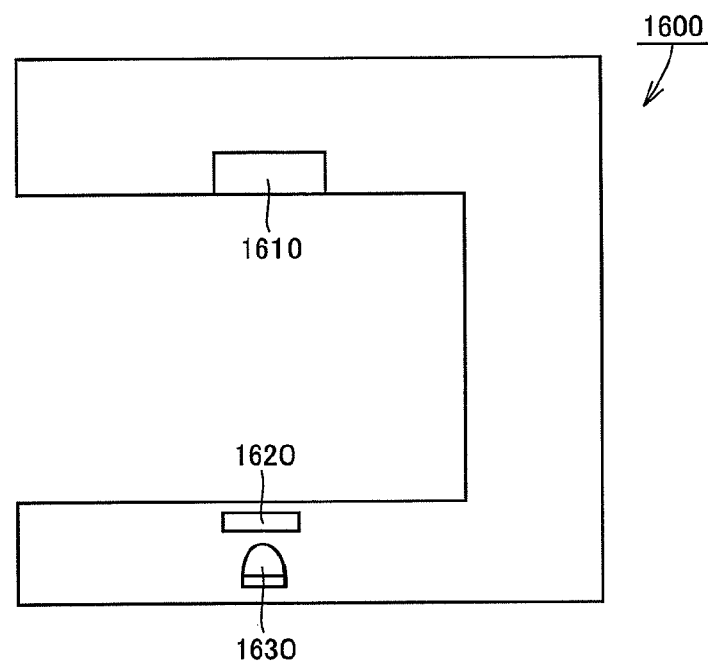
FIG. 20B is a side sectional view of the discrimination filtering device.

A configuration of the discrimination filtering device according to the present embodiment will be described with reference to FIGS. 20A and 20B. FIGS. 20A and 20B are diagrams representing a configuration of discrimination filtering device 1600.

FIG. 20A shows an appearance of discrimination filtering device 1600 according to the second embodiment. FIG. 20B is a side sectional view of discrimination filtering device 1600.

Referring to FIG. 20A or FIG. 20B, discrimination filtering device 1600 includes a plurality of light receiving elements 1610.1 to 1610.N, a plurality of filters 1620.1 to 1620.N, a light source 1630, an indicator 1640, and a buzzer 1645.

Referring to FIG. 20A, discrimination filtering device 1600 takes a rectangular shape with one side absent (u-shape in sideways position). Light receiving element 1610 and filter 1620 are arranged along opposite sides of the rectangle.

Each of a plurality of light receiving elements 1610.1 to 1610.N detects light and outputs an electric signal corresponding to the detected amount of light. In the case where light receiving elements 1610.1 to 1610.N each do not have to be distinguished, they will be generically referred to as light receiving element 1610. In the present embodiment, a photodiode that is one type of point sensor is used as light receiving element 1610. A photodiode is advantageous in that it is inexpensive as compared to a light receiving element such as a CCD.

Each of plurality of filters 1620.1 to 1620.N allows the passage of an electromagnetic wave of a predetermined wavelength region, and blocks the electromagnetic wave of other wavelength region. In the case where filters 1620.1 to 1620.N each do not have to be distinguished, they will be generically referred to as filter 1620. In the present embodiment, it is assumed that filter 1620 is a bandpass filter. The pass band of each filter 1620 is designed by a method similar to that of the first embodiment, according to the components required for discrimination.

Discrimination filtering device 1600 includes a number of filters 1620 and a number of light receiving elements 1610, corresponding to the number of the components that are the subject of discrimination. As appreciated from the description in the first embodiment, discrimination filtering device 1600 can discriminate one type of component using the detection results of light passed through two filters 1620 having different pass bands. Therefore, at least two filters 1620 are required.

In order to distinguish M (M is an integer of 2 or above) types of components, 2M filters 1620 are sufficient. In the case where the pass band is identical for filters 1620 used in different discrimination (identification filter or normalization filter), the number of filters 1620 may be less than 2M.

Discrimination filtering device 1600 includes filters 1620, identical in number to that of light receiving elements 1610. Therefore, the configuration of discrimination filtering device 1600 is rendered simple as compared to that of the first embodiment. Discrimination filtering device 1600 does not have to mechanically switch the filters. Moreover, discrimination filtering device 1600 does not have to include an optical element such as a beam splitter.

Light source 1630 emits light. Light source 1630 is arranged at the rear side of filter 1620. Namely, the light output from light source 1630 passes through filter 1620 to enter light receiving element 1610.

Although not explicitly shown in FIGS. 20A and 20B, light source 1630 includes a plurality of LEDs 1630.1 to 1630.N. Namely, light source 1630 is an LED light source. LEDs 1630.1 to 1630.N are arranged at the rear side of filters 1620.1 to 1620.N, respectively.

The LED is advantageous in that it does not generate so much heat as compared to other light sources such as a halogen lamp. The light from the LED has sufficient brightness for discrimination of an object. Particularly, discrimination filtering device 1600 is covered with a light-blocking material, as previously mentioned, in the present embodiment. Accordingly, the amount of light output from light source 1630 does not have to be increased so much.

For light source 1630, another type of light source may be used instead of the LED light source. It is to be noted that light source 1630 must output light over a wider range than the pass band of the filter. Therefore, it is not appropriate to employ laser whose wavelength of output light may be restricted as a light source. In other words, a light source of wider line width is to be prepared for discrimination of an object in the present embodiment. It is not necessary to narrow the line width of the light source.

Indicator 1640 outputs light according to the discrimination result. For example, indicator 1640 outputs light when discrimination filtering device 1600 indicates a discrimination result differing from that of a general one. Such an event includes the case where the specimen contains impurities. Indicator 1640 includes, but not particularly limited to, an LED, an incandescent lamp, or the like.

Buzzer 1645 outputs a sound corresponding to the discrimination result. For example, buzzer 1645 issues a sound (warning sound) when discrimination filtering device 1600 indicates a discrimination result differing from that of a general one.

Indicator 1640 and buzzer 1645 are examples of a device for providing the discrimination result. Discrimination filtering device 1600 may output the discrimination result through a device other than indicator 1640 and buzzer 1645. For example, discrimination filtering device 1600 may include, instead or in addition, a monitor to display the discrimination results in characters, numerics, graphics, or the like.

Figure 21:
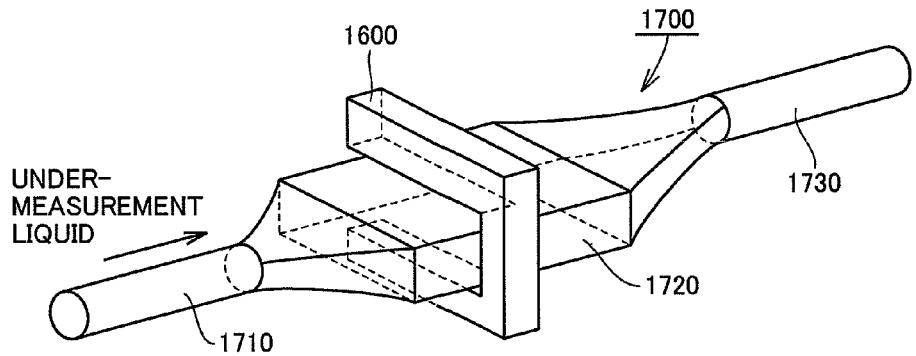
FIG. 21 represents a manner of usage of a discrimination filtering device according to the second embodiment.

A manner of usage of discrimination filtering device 1600 will be described with reference to FIG. 21. FIG. 21 is a diagram representing a manner of usage of discrimination filtering device 1600. In FIG. 21, the manner of usage of discrimination filtering device 1600 in discriminating a specimen in tube 1700 is illustrated.

Tube 1700 includes a round tube 1710, a square tube 1720, and a round tube 1730. Round tube 1710 (or round tube 1730) is smoothly connected with square tube 1720. The specimen (the liquid subjected to measurement) sequentially flows through tube 1700 in the order of round tube 1710, square tube 1720, and round tube 1730.

Discrimination filtering device 1600 is arranged to sandwich square tube 1720. Therefore, light receiving element 1610, filter 1620, and LED 1630 of discrimination filtering device 1600 are aligned one-dimensionally in the flowing direction of the specimen.

Although not shown, the user covers tube 1700 and discrimination filtering device 1600 with a blackout curtain, a dark box, black resin, or the like during specimen measurement. Alternatively, the user may carry out the measurement in a dark room.

Figure 22:
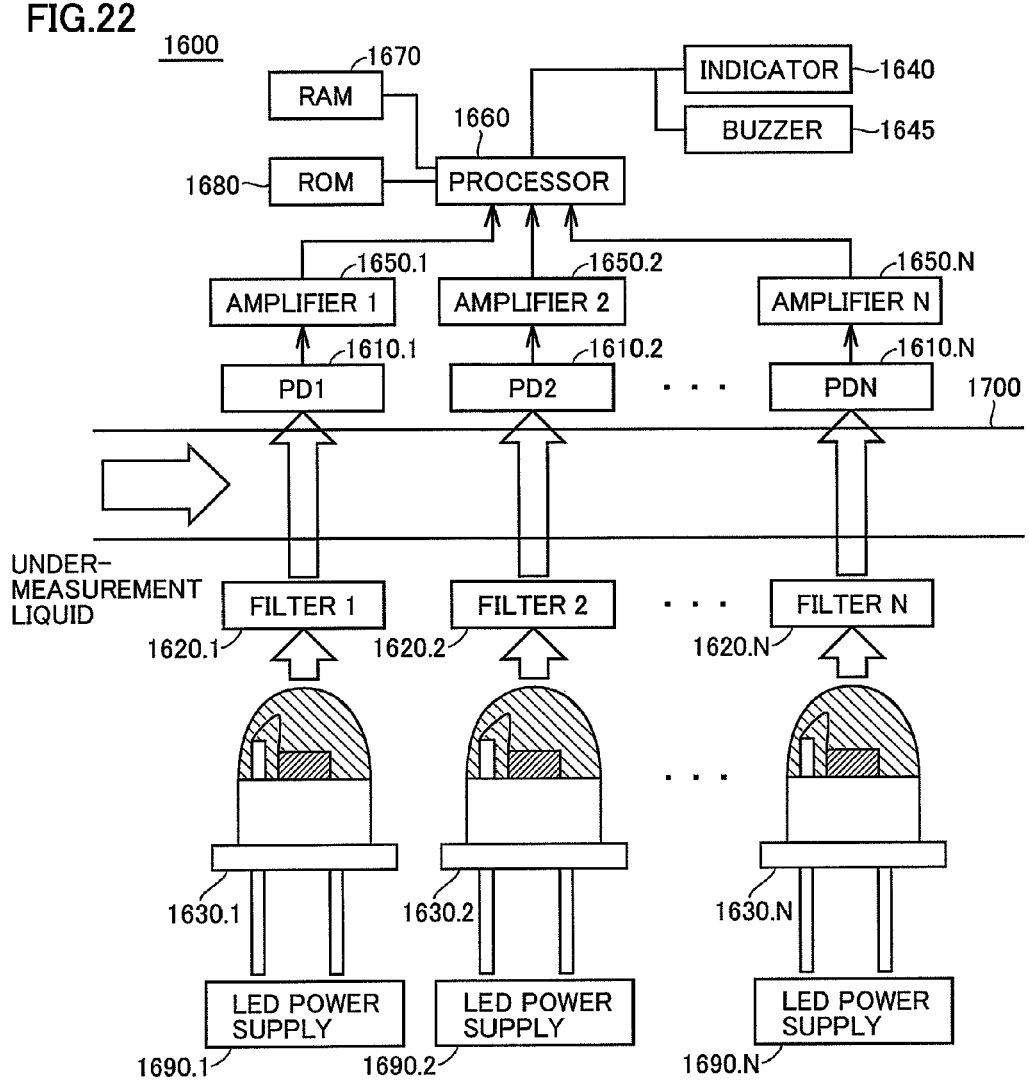
FIG. 22 shows in detail a configuration of the discrimination filtering device according to the second embodiment.

The configuration of discrimination filtering device 1600 will be described in more detail with reference to FIG. 22. FIG. 22 represents the details of a configuration of discrimination filtering device 1600.

Referring to FIG. 22, discrimination filtering device 1600 includes light receiving elements 1610.1 to 1610.N, filters 1620.1 to 1620.N, LEDs 1630.1 to 1630.N, indicator 1640, buzzer 1645, amplifiers 1650.1 to 1650.N, a processor 1660, a RAM 1670, a ROM 1680, and LED light sources 1690.1 to 1690.N.

FIG. 22 corresponds to a view of the arrangement of light receiving elements 1610.1 to 1610.N, filters 1620.1 to 1620.N, and LEDs 1630.1 to 1630.N in the direction orthogonal to the moving direction of the under-measurement liquid. The actual arrangement of other constituent elements is irrelevant to that shown in FIG. 22.

Light receiving elements 1610.1-1610.N detect LED light output from LED 1630.1 to 1630.N and passed through filters 1620.1 to 1620.N, respectively. Namely, each light receiving element 1610.$k$ ($k$=1 to N) detects only the LED light output from LED 1630.$k$.

By the spread of the LED light itself output from LED 1630 and the scattering of the LED light caused by the specimen, the LED light output from one LED 1630 will expand slightly. The two adjacent light receiving elements 1610 are preferably arranged farther from the spread of the LED light. The designer of discrimination filtering device 1600 may design the distance of light receiving elements 1610 appropriately according to the distance between light receiving element 1610 and filter 1620 (or, the thickness of square tube 1720), the characteristic of LED 1630, the nature of the specimen, and the like.

Amplifier 1650.$k$ ($k$=1 to N) amplifies the light detection signal (electric signal) of light receiving element 1610.$k$. Amplifier 1650.$k$ provides the amplified light detection signal to processor 1660.

Processor 1660 performs componential analysis of a specimen based on the light detection signal (amplified light detection signal) of each light receiving element 1610. Processor 1660 performs component discrimination based on light detection signals from a plurality of light receiving elements 1610 corresponding to components to be distinguished. Processor 1660 provides a control signal based on the discrimination result to indicator 1640 and buzzer 1645. Processor 1660 includes, but not particularly limited to, a general purpose CPU.

RAM 1670 temporarily stores the processed result from processor 1660. Namely, RAM 1670 functions as a working memory. ROM 1680 stores data required for componential analysis (teaching data, discrimination function, program, and the like). A data readable and writable memory device such as a hard disk or flash memory may be used instead of ROM 1680. Further, processor 1660, RAM 1670, and ROM 1680 may be replaced by a microcomputer.

LED power supplies 1690.1 to 1690.N supply power to LEDs 1630.1 to 1630.N, respectively. Each of LED power supplies 1690.1 to 1690.N initiates or ends power supply according to the switching of, for example, a power supply switch.

First Modification

The configuration of a discrimination filtering device is not limited to that described above. A configuration of a discrimination filtering device 1600# according to a first modification will be described hereinafter.

Figure 23A:
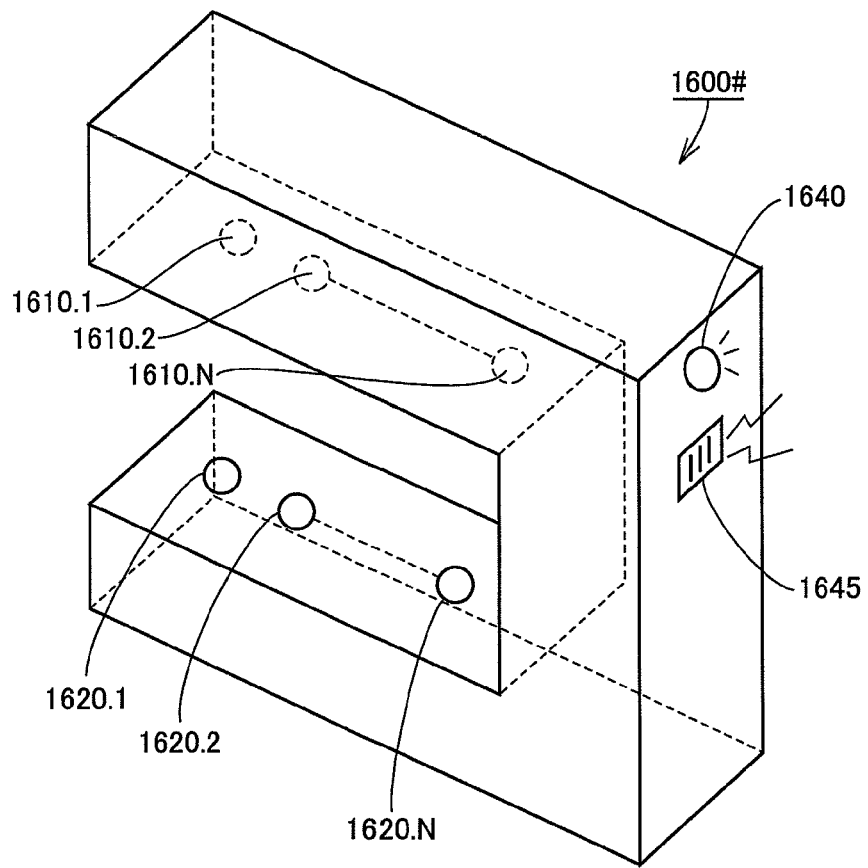
FIG. 23A represents an appearance of a discrimination filtering device according to a first modification.
Figure 23B:
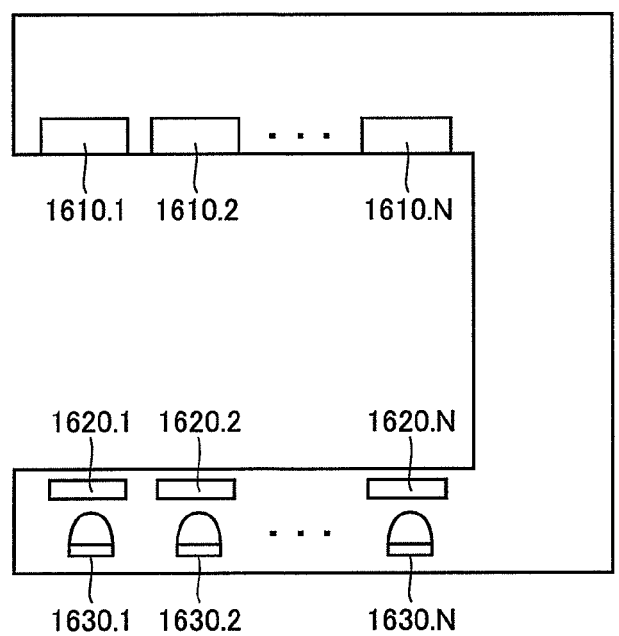
FIG. 23B is a side sectional view of the discrimination filtering device according to the first modification.

FIGS. 23A and 23B represent a configuration of discrimination filtering device 1600# according to the first modification. FIG. 23A represents an appearance of discrimination filtering device 1600# according to the first modification. FIG. 23B is a side sectional view of discrimination filtering device 1600#.

The difference between discrimination filtering device 1600 and discrimination filtering device 1600# lies in the arrangement of light receiving element 1610, filter 1620, and LED 1630. Specifically, the direction of alignment of light receiving element 1610, filter 1620, and LED 1630 of discrimination filtering device 1600# differs 90 degrees from the direction of alignment of light receiving element 1610, filter 1620, and LED 1630 of discrimination filtering device 1600.

Discrimination filtering device 1600# is used in a manner similar to that of discrimination filtering device 1600 (refer to FIG. 21). Therefore, light receiving element 1610, filter 1620, and LED 1630 of discrimination filtering device 1600# are aligned one-dimensionally in a direction orthogonal to the flowing direction of the specimen.

By the above-described arrangement of light receiving element 1610, filter 1620, and LED 1630, discrimination filtering device 1600# can be formed more compact than discrimination filtering device 1600. Alternatively, discrimination filtering device 1600# may include more light receiving elements 1610, filters 1620, and LEDs 1630 than in discrimination filtering device 1600.

The specific configuration of discrimination filtering device 1600# is similar to that of discrimination filtering device 1600 shown in FIG. 22 except for the arrangement of light receiving element 1610, filter 1620, and LED 1630. Therefore, description thereof will not be repeated.

Second Modification

Discrimination filtering device 1600 and discrimination filtering device 1600# has filter 1620 located between LED 1630 and the specimen. The location of filter 1620 is not limited thereto, as long as filter 1620 is located between LED 1630 and light receiving element 1610.

A discrimination filtering device 2400 according to a second modification includes filter 1620 between the site where the specimen is located and light receiving element 1610. Specifically, filter 1620 is arranged immediately before light receiving element 1610.

Figure 24:
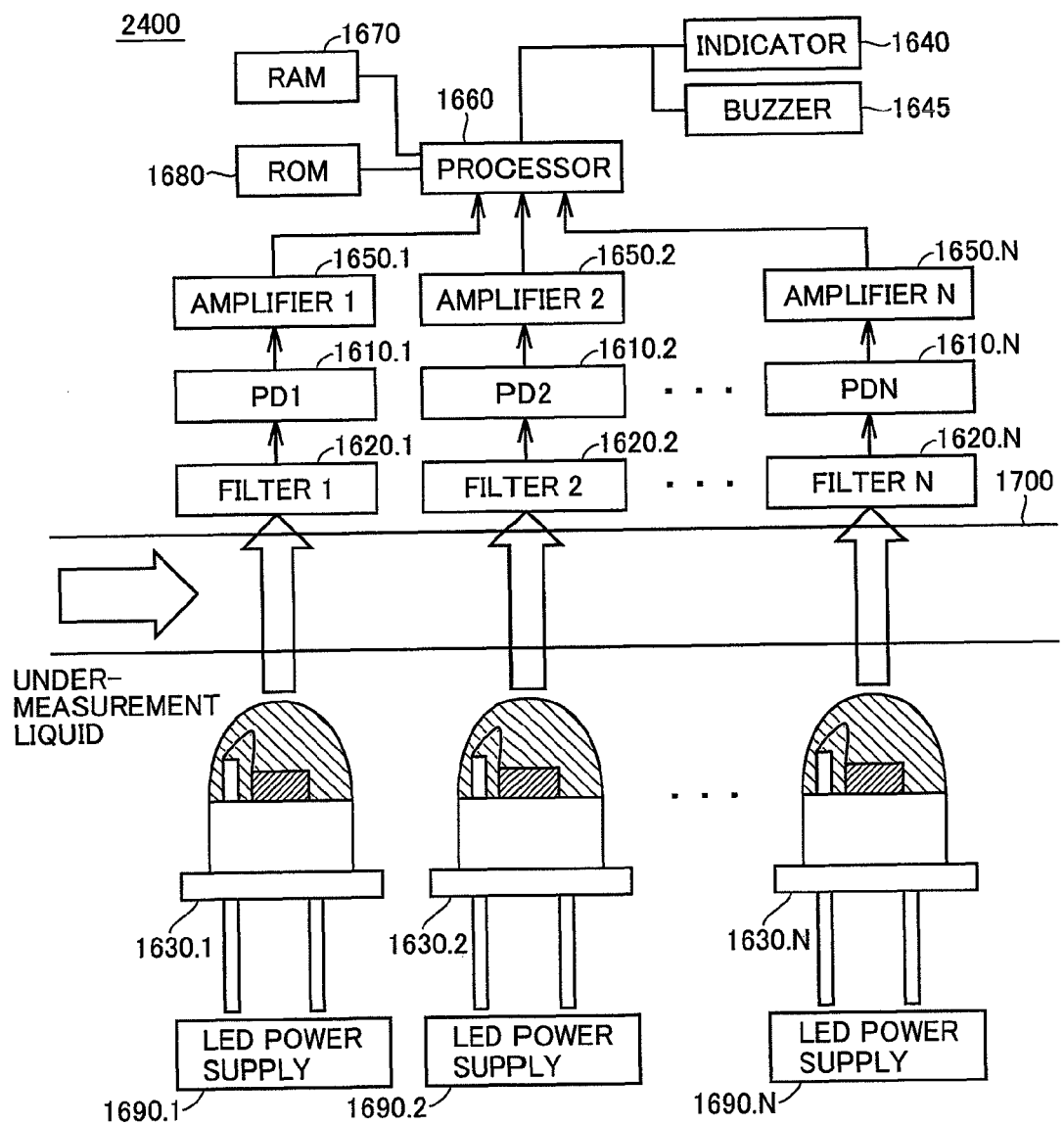
FIG. 24 represents a configuration of a discrimination filtering device according to a second modification.

A configuration of discrimination filtering device 2400 according to the second modification is shown in FIG. 24. FIG. 24 represents a configuration of discrimination filtering device 2400 according to the second embodiment. FIG. 24 corresponds to a view of the arrangement of light receiving elements 1610.1 to 1610.N, filters 1620.1 to 1620.N and LEDs 1630.1 to 1630.N in a direction orthogonal to the moving direction of the under-measurement liquid, similar to FIG. 22. The actual arrangement of other constituent elements is irrelevant to that shown in FIG. 24.

Light receiving element 1610, filter 1620, and LED 1630 of discrimination filtering device 2400 are aligned one-dimensionally in the flowing direction of the specimen, likewise with those of discrimination filtering device 1600. However, the arrangement of light receiving element 1610, filter 1620, and LED 1630 are not limited thereto. They may be arranged one-dimensionally in a direction orthogonal to the flowing direction of the specimen, as in discrimination filtering device 1600#.

By the configuration in which filter 1620 is arranged immediately before light receiving element 1610, the number of LEDs 1630 can be reduced. In the case where the band of light output from LED 1630 includes the pass band of each filter 1620, LEDs 1630.1 to 1630.N may be replaced with a single LED 1630. In the case where the radiation range of the LED light from one LED 1630 is smaller than filter 1620, several LEDs 1630, instead of one, may be employed.

Moreover, if each light receiving element 1610 detects light from a common LED 1630, light receiving elements 1610 may be arranged close to each other. Accordingly, discrimination filtering device 2400 can be formed more compact. Alternatively, discrimination filtering device 2400 may have many light receiving elements 1610 installed to allow the analysis of more components.

Third Modification

The above-described discrimination filtering device 1600 (or discrimination filtering device 1600#, discrimination filtering device 2400) may have the plurality of filters 1620 replaced with a filter array including a plurality of filters. Further, the plurality of light receiving elements 1610 may be replaced with a light receiving element array including a plurality of light receiving elements.

As a third modification, a discrimination filtering device 2500 including a filter array and the light receiving element array will be described. Discrimination filtering device 2500 is a partially modified version of discrimination filtering device 2400 of the second modification.

Figure 25:
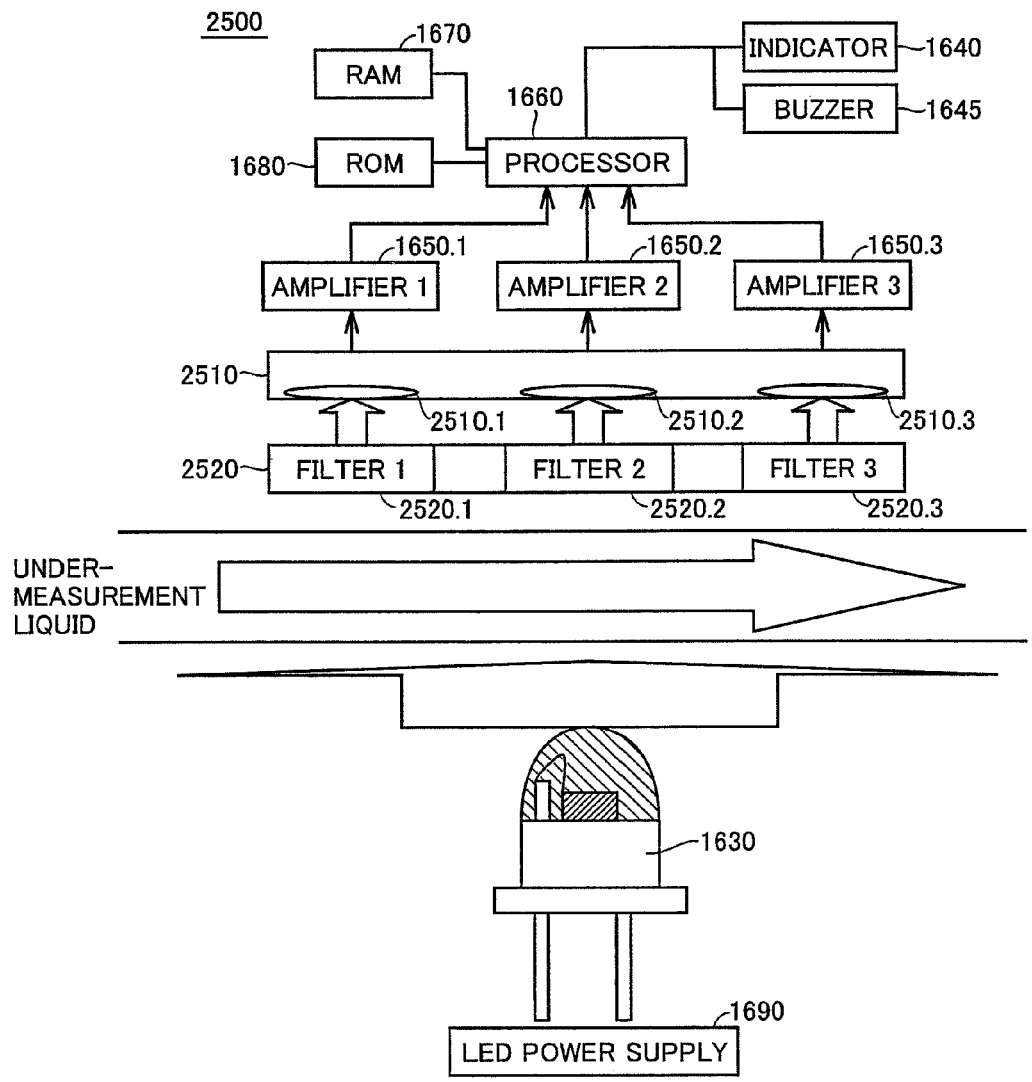
FIG. 25 represents a configuration of a discrimination filtering device according to a third modification.

A configuration of discrimination filtering device 2500 is shown in FIG. 25. FIG. 25 represents a configuration of discrimination filtering device 2500 according to the third modification. FIG. 25 corresponds to a view of the arrangement of light receiving elements 1610.1 to 1610.N, filters 1620.1 to 1620.N and LEDs 1630.1 to 1630.N in a direction orthogonal to the moving direction of the under-measurement liquid, similar to FIGS. 22 and 24. The actual arrangement of other constituent elements is irrelevant to that shown in FIG. 25.

Referring to FIG. 25, discrimination filtering device 2500 includes a light receiving element array 2510 instead of light receiving elements 1610.1 to 1610.N in discrimination filtering device 2400. Discrimination filtering device 2500 also includes a filter array 2520 instead of filters 1620.1 to 1620.N in discrimination filtering device 2400. Further, discrimination filtering device 2500 includes one, not a plurality of, LED 1630 and LED power supply 1690.

Light receiving element array 2510 includes a light receiving element 2510.$k$ ($k=1$ to N). In the present embodiment, it is assumed that light receiving element array 2510 is a PD array. Namely, each light receiving element 2510.$k$ is a PD, similar to light receiving element 1610 in discrimination filtering device 2400 and the like.

Filter array 2520 includes a filter 2520.$k$ ($k=1$ to N). The pass band of each filter 2520.$k$ is designed according to the object of discrimination, similar to the pass band of filter 1620 in discrimination filtering device 2400.

The distance of light receiving elements 2510.$k$ is designed matching the distance of filters 2520.$k$. Namely, the distance of light receiving elements 2510.$k$ is determined such that the light output from LED 1630 and passed through filter 2520.$k$ enters light receiving element 2510.$k$.

By virtue of the usage of filter array 2520 and light receiving element array 2510, discrimination filtering device 2500 is more readily fabricated, as compared with discrimination filtering device 2400 and the like.

When a plurality of light sources are required for the discrimination filtering device, a power source array including a plurality of light sources may be employed. Particularly, in the case where the positional relationship between a filter and each light source is restricted such as in discrimination filtering device 1600 shown in FIG. 22, the usage of a power source array facilitates fabrication of a discrimination filtering device.

Fourth Modification

The above description is based on the case where one discrimination filtering device effects radiation of light to a specimen, detection of light passed through a specimen, discrimination of a specimen based on the light detection result, and providing the discrimination result. These operations may be implemented by a combination of a plurality of devices.

Figure 26:
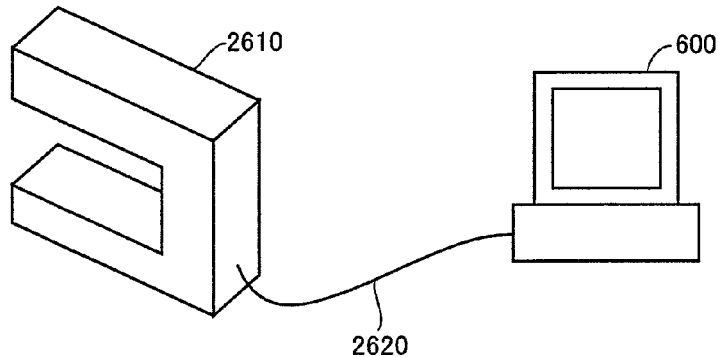
FIG. 26 represents a configuration of a discrimination filtering system.

The fourth modification is based on a discrimination filtering system 2600 for specimen discrimination. A configuration of discrimination filtering system 2600 is shown in FIG. 26. FIG. 26 represents a configuration of discrimination filtering system 2600.

Referring to FIG. 26, discrimination filtering system 2600 includes a specimen measurement device 2610, a computer 600, and a cable 2620.

Specimen measurement device 2610 has a configuration similar to that of discrimination filtering device 1600. Specimen measurement device 2610 includes a plurality of LEDs, a plurality of filters, and a plurality of light receiving elements located similarly to, but not restricted to, those in discrimination filtering device 1600. The LED, filter, and light receiving element may be arranged as shown in the first to fourth modifications.

Specimen measurement device 2610 outputs the light detection result of each light receiving element to an external source. Specimen measurement device 2610 itself does not perform specimen discrimination based on the light detection result. Specimen measurement device 2610 also does not output the discrimination result through a buzzer and/or indicator.

Cable 2620 connects specimen measurement device 2610 with computer 600. Cable 2620 transmits the light detection result output from specimen measurement device 2610 to computer 600. Cable 2620 includes, but not restricted to, an USB cable or the like.

Specimen measurement device 2610 and computer 600 do not have to be connected directly by cable 2620. Specimen measurement device 2610 and computer 600 may be connected through a network, or through radio.

3. Process Flow

Figure 27:
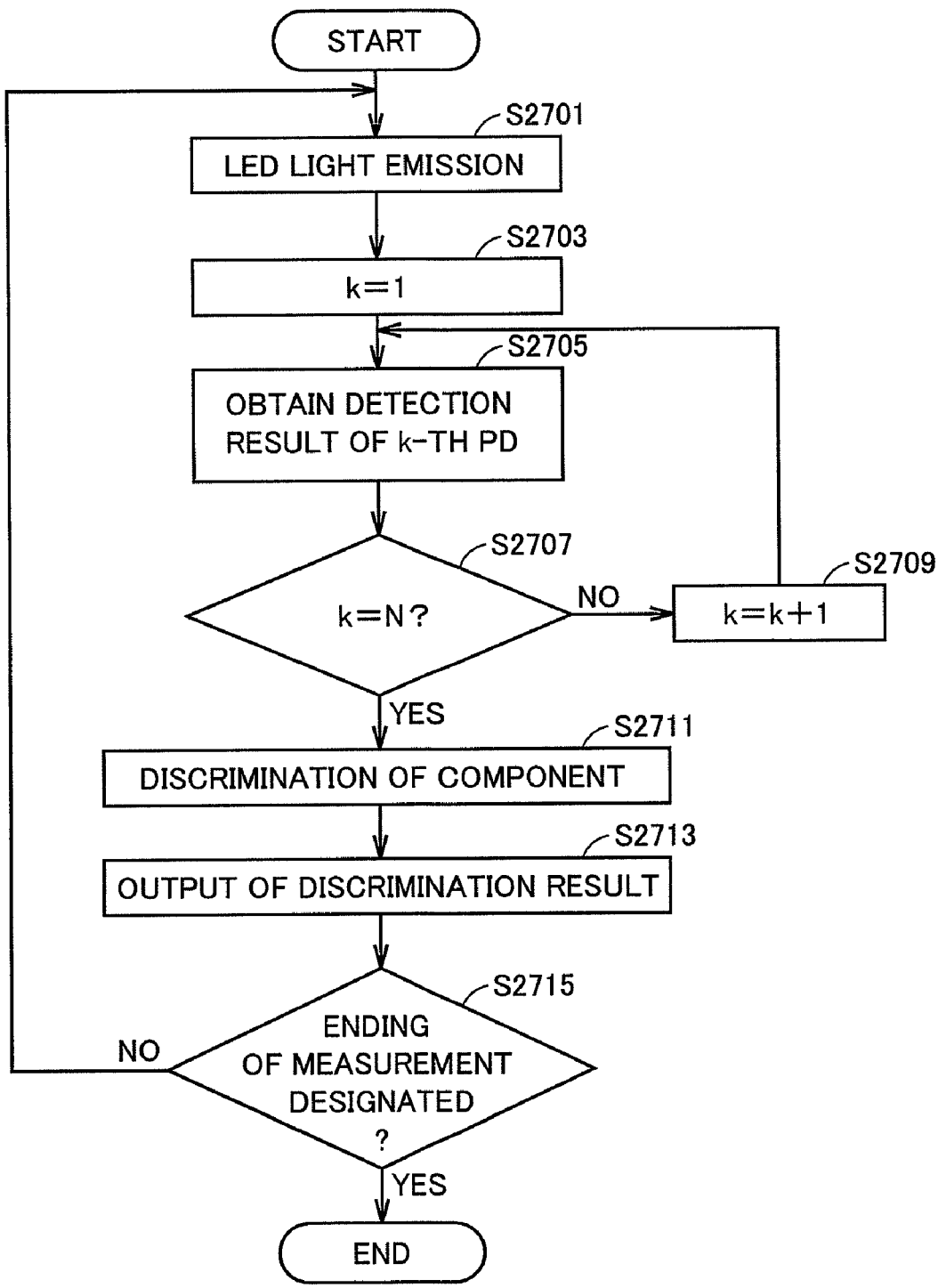
FIG. 27 is a flowchart of the flow of processes carried out by the discrimination filtering device.

The flow of the processes carried out by discrimination filtering device 1600 in specimen discrimination will be described with reference to FIG. 27. FIG. 27 is a flowchart of the flow of processes carried out by discrimination filtering device 1600.

At step S2701, each LED 1630.$k$ initiates light output. Each LED 1630.$k$ outputs light according to the power supplied from LED power supply 1690.$k$. Each LED 1630.$k$ initiates light output in response to, for example, depression of a switch of LED power supply 1690.$k$ by the user.

At step S2703, processor 1660 initializes a parameter k specifying a light receiving element (or filter). Here, it is assumed that the initial value of k is 1.

At step S2705, processor 1660 obtains the light detection result of light receiving element 1610.$k$. Processor 1660 stores the obtained light detection result in RAM 1670.

At step S2707, processor 1660 determines whether k=N (N: the number of light receiving elements 1610). When k=N (YES at step S2707), processor 1660 proceeds to the process of step S2711. When k is not N (NO at step S2707), processor 1660 proceeds to step S2709 to increment the value of k. Then, processor 1660 returns to the process of step S2705.

At step S2711, processor 1660 performs discrimination of the components included in the specimen. Specifically, processor 1660 first selects a set of light receiving elements 1610.$k$ corresponding to the component to be distinguished. Then, processor 1660 takes the logarithm of the light detection result of each selected light receiving element 1610.$k$. Next, processor 1660 substitutes the logarithm of the light detection result into the discrimination function. Processor 1660 distinguishes the specimen based on whether the result of substitution is positive or negative.

At step S2713, processor 1660 controls each element in discrimination filtering device 1600 to cause output of the discrimination result. Specifically, processor 1660 controls indicator 1640 and buzzer 1645.

For example, processor 1660 determines whether the discrimination result obtained at step S2711 matches the "proper" discrimination result. Processor 1660 causes indicator 1640 to emit light or buzzer 1645 to output a sound according to whether the results match or not. The "proper" discrimination result is given in advance. For example, it is assumed that the designer of discrimination filtering device 1600 prestores the proper discrimination result in ROM 1680. Alternatively, the user may be allowed to set the proper discrimination result.

In the case where discrimination filtering device 1600 incorporates another result output device (a monitor or the like), processor 1660 may control the relevant result output device to cause output of the discrimination result at step S2711.

At step S2715, processor 1660 determines whether a measurement ending designation has been received or not. For example, processor 1660 takes the depression of a certain switch at discrimination filtering device 1600 as the designation of ending measurement.

When a measurement ending designation is received (YES at step S2715), processor 1660 ends the specimen discrimination process. When a measurement ending designation is not received (NO at step S2715), processor 1660 repeats the process from step S2701.

By the processing set forth above, discrimination filtering device 1600 can continuously distinguish a component in a fluid flowing through tube 1700 in real time. Therefore, the user of discrimination filtering device 1600 can continue to monitor the component of the fluid in real time.

Discrimination filtering device 1600 can also distinguish a component of an immobile object (provided that the object allows light to pass through). In this case, discrimination filtering device 1600 does not have to repeatedly distinguish the components. Therefore, discrimination filtering device 1600 may end the discrimination process after step S2713 without performing the process of step S2715.

Discrimination filtering device 1600#, discrimination filtering device 2400 and discrimination filtering device 2500 perform processing similar to that described above. The processing in each of these devices will not be repeated here.

Discrimination filtering system 2600 also performs processing similar to that described above, provided that CPU 610 of computer 600, not processor 1660, performs the processes from step S2703 to step S2715. Further, the discrimination result is output from monitor 670 of computer 600 at step S2715.

Modification of Process

Figure 28:
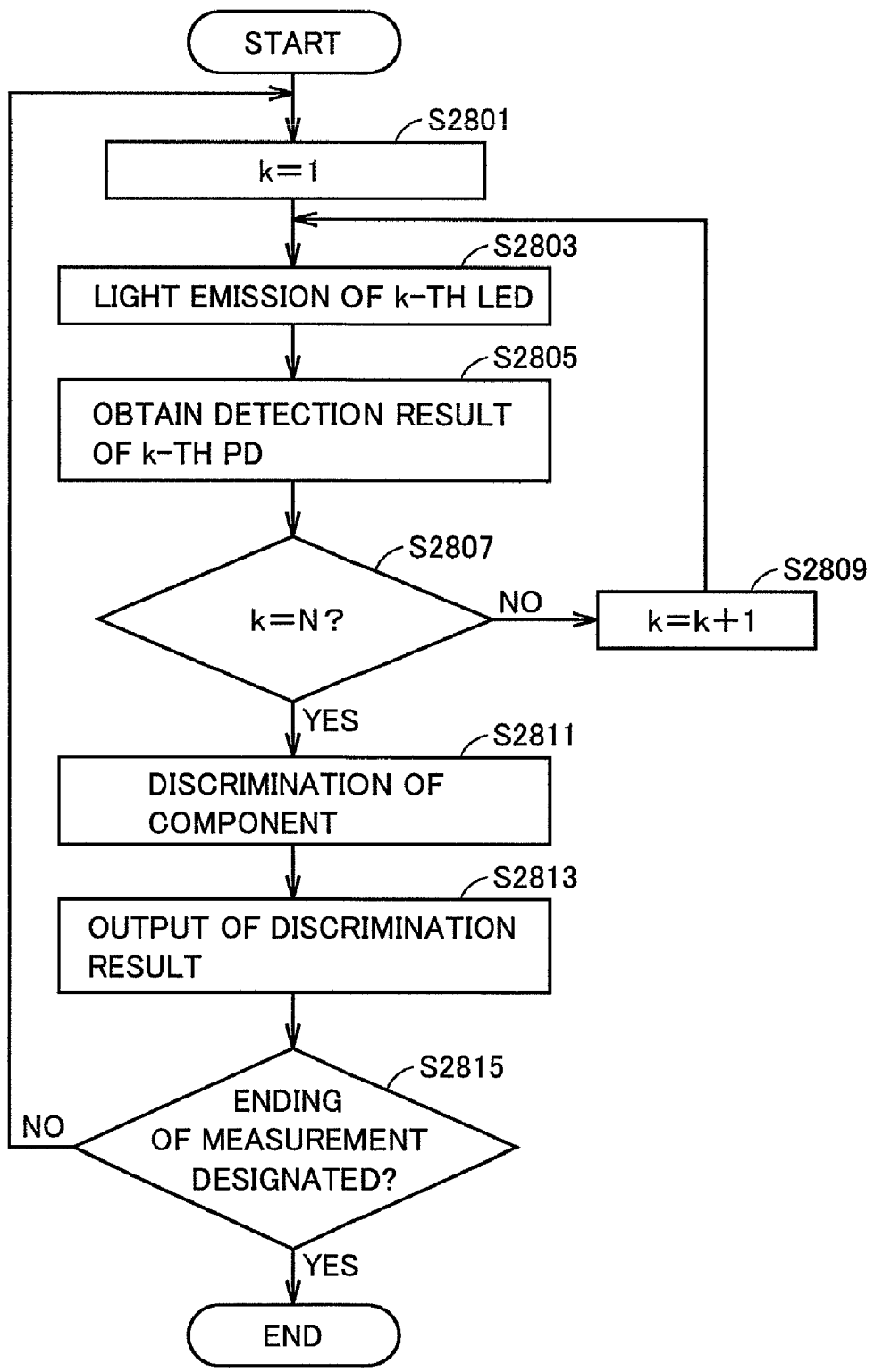
FIG. 28 is a flowchart of the flow of processes according to a modification carried out by the discrimination filtering device.

In the process flow set forth above, discrimination filtering device 1600 had all LEDs 1630.1 to 1630.N lit during specimen discrimination. Alternatively, discrimination filtering device 1600 may have LEDs 1630.1 to 1630.N sequentially lit one by one. The flow of the processes carried out by discrimination filtering device 1600 in such a case will be described with reference to FIG. 28. FIG. 28 represents a flowchart of the flow of the processes according to a modification carried out by the discrimination filtering device.

At step S2801, processor 1660 initializes parameter k specifying a light receiving element, filter, and LED. Here, it is assumed that the initial value of k is 1.

At step S2803, processor 1660 controls LED power supply 1690.$k$ to cause LED 1630.$k$ to output light. Processor 1660 controls LED power supply 1690.$j$ such that another LED 1630.$j$ ($j \neq k$) does not output light.

At step S2805, processor 1660 obtains the light detection result of light receiving element 1610.$k$. Processor 1660 stores the obtained light detection result in RAM 1670. The light detection result corresponds to the amount of light output from LED 1630.$k$ and passed through filter 1620.$k$ and the specimen.

At step S2807, processor 1660 determines whether k=N (N: the number of light receiving elements 1610). When k=N (YES at step S2807), processor 1660 proceeds to step S2811. When k is not N (NO at step S2807), processor 1660 proceeds to step S2809 to increment the value of k. Then, processor 1660 returns to the process from step S2803.

The processes of step S2811 and step S2813 are similar to those of step S2711 and step S2713 previously described. Therefore, detailed description thereof will not be repeated.

At step S2815, processor 1660 determines whether a measurement ending designation is received or not. For example, processor 1660 assumes that ending the measurement is designated by depression of a certain switch at discrimination filtering device 1600.

When designation of ending the measurement is received (YES at step 2815), processor 1660 ends the specimen discrimination process. When designation of ending the measurement is not received (NO at step S2815), processor 1660 repeats the process from step S2801.

According to the process of the present modification, the detection result of each light receiving element 1610.$k$ corresponds to the light from LED 1630.$k$ corresponding to light receiving element 1610.$k$. The light from another light receiving element 1610.$j$ will not affect the detection result of light receiving element 1610.$k$. Therefore, according to the processing of the present modification, the detection accuracy can be improved. Further, light receiving element 1610, filter 1620, and LED 1630 may be arranged in close density according to the process in the present modification.

Discrimination filtering device 1600#, discrimination filtering device 2400, discrimination filtering device 2500, or discrimination filtering system 2600 may carry out the processing similar to that of the present modification.

Miscellaneous

It will be understood that a configuration based on an appropriate combination of each of the embodiments or modifications of the embodiments is encompassed within the scope of the present invention.

It should be understood that the embodiments disclosed herein are illustrative and non-restrictive in every respect. The scope of the present invention is defined by the appended claims, rather than the description set forth above, and all changes that fall within limits and bounds of the claims, or equivalence thereof are intended to be embraced by the claims.

INDUSTRIAL APPLICABILITY

The present invention can be used to determine how much the river is frozen from above a bridge, for example. Furthermore, the present invention is applicable to the measurement of moisture content of the skin. In addition, the present invention may be used widely for non-destructive evaluation of compositional distribution in the industrial field related to the usage of water such as identifying the quality between water component from another component (mineral, nitrogen, starch, amino acid) in agriculture products, monitoring the water content in fiber, the mixed state of solutions, monitoring phosphorus in seawater, identification between sludge water and petroleum component, discrimination measurement between water component and another component (for example, sebum, amino acid, collagen) of a living body (outside, inside), measurement of water component in hair, identification of food composition, rapid determination of virus infection, border inspection of imported infectious disease in food, inorganic ingredient evaluation of concentrated seawater, evaluation of seawater component and plant distribution from a satellite, identification and evaluation of moisture and salt content in concrete, and the like. The present invention is also applicable to the monitoring evaluation over time thereof.

The invention claimed is:

1. A discrimination filtering device comprising:
    a first filter with a first pass band based on a spectrum for a plurality of types of specimens whose classification is identified in advance, the first pass band adapted to lower the probability of a specimen belonging to a group being erroneously determined as belonging to another group,
    a second filter with a second pass band encompassing said first pass band,
    a detection unit for detecting an electromagnetic wave output from an object of interest and passed through one of said first filter and said second filter to output a first signal and a second signal corresponding to intensity of the electromagnetic wave from said object of interest, and
    an analysis unit for performing a discriminant analysis of said object of interest based on said first signal normalized by an integral of said second signal.

2. The discrimination filtering device according to claim 1, wherein said analysis unit performs said discriminant analysis of said object of interest based on a difference between a logarithm of an integral of said first signal and the logarithm of the integral of said second signal.

3. The discrimination filtering device according to claim 1, wherein said analysis unit performs said discriminant analysis of said object of interest based on a value obtained by substituting said first signal and said second signal into a discrimination function determined based on said first pass band and said second pass band.

4. The discrimination filtering device according to claim 1, wherein said first pass band and said second pass band include a near infrared region.

5. The discrimination filtering device according to claim 1, wherein said analysis unit identifies two or more types of substances classified by type.

6. The discrimination filtering device according to claim 1, wherein said analysis unit identifies water from another substance.

7. The discrimination filtering device according to claim 1, wherein said analysis unit evaluates and identifies a water content at a surface of or inside a substance.

8. The discrimination filtering device according to claim 1, further comprising a wave source for emitting an electromagnetic wave,
    wherein said detection unit detects an electromagnetic wave output from said object of interest receiving said electromagnetic wave output from said wave source.

9. The discrimination filtering device according to claim 8, wherein said wave source includes an LED.

10. The discrimination filtering device according to claim 8, wherein said detection unit detects an electromagnetic wave output from said wave source and passed through said object of interest.

11. The discrimination filtering device according to claim 8, wherein said detection unit detects an electromagnetic wave output from said wave source and reflected from said object of interest.

12. The discrimination filtering device according to claim 1, wherein said detection unit includes at least one element converting an electromagnetic wave into an electric signal.

13. The discrimination filtering device according to claim 1, wherein said detection unit includes a plurality of elements, each converting an electromagnetic wave into an electric signal, said plurality of elements being aligned one-dimensionally.

14. The discrimination filtering device according to claim 1, wherein said detection unit includes an image sensing element having elements aligned two-dimensionally, each element converting an electromagnetic wave into an electric signal.

15. A discrimination method of an object of interest, comprising the steps of:
    detecting an electromagnetic wave output from said object of interest and passed through a first filter with a first pass band to output a first signal corresponding to intensity of the electromagnetic wave passed through said first filter,
    detecting an electromagnetic wave output from said object of interest and passed through a second filter with a second pass band encompassing said first pass band to output a second signal corresponding to intensity of the electromagnetic wave passed through said second filter, and
    performing a discriminant analysis of said object of interest based on said first signal normalized by an integral of said second signal,
    wherein the first pass band is based on a spectrum for a plurality of types of specimens whose classification is identified in advance and is adapted to lower the probability of a specimen belonging to a group being erroneously determined as belonging to another group.

16. A designing method of filters for a discrimination filtering device, comprising the steps of:
    setting a transmission property for each of a plurality of filters,
    generating, from the set transmission property and a teaching spectrum of a plurality of samples, a discrimination function used in discriminating an object of interest by said discrimination filtering device,
    calculating an error rate of erroneously discriminating the sample when said discrimination function is used,
    modifying said transmission property,
    regenerating said discrimination function from the modified transmission property and said teaching spectrum,
    calculating said error rate for the regenerated discrimination function, and
    obtaining said transmission property providing the smallest error rate among the set transmission property and modified transmission property.

17. The designing method of filters for the discrimination filtering device according to claim 16, wherein
    said teaching spectrum includes a spectrum of a near infrared region, and
    said modified transmission property includes a transmission property with a pass band of the near infrared region.

* * * * *